US012778446B2

(12) United States Patent
Shouldice et al.

(10) Patent No.: US 12,778,446 B2
(45) Date of Patent: Nov. 3, 2026

(54) SYSTEMS AND METHODS FOR DETERMINING A HEALTH CONDITION ON A DEVICE LOCAL TO A RESPIRATORY SYSTEM USER

(71) Applicant: ResMed Inc., San Diego, CA (US)

(72) Inventors: Redmond Shouldice, Dublin (IE); Benjamin Peter Johnston, Sydney (AU)

(73) Assignee: ResMed Inc., San Diego, CA (US)

( * ) Notice: Subject to any disclaimer, the term of this patent is extended or adjusted under 35 U.S.C. 154(b) by 783 days.

(21) Appl. No.: 18/007,343

(22) PCT Filed: Jul. 28, 2021

(86) PCT No.: PCT/IB2021/056885
§ 371 (c)(1),
(2) Date: Jan. 30, 2023

(87) PCT Pub. No.: WO2022/024010
PCT Pub. Date: Feb. 3, 2022

(65) Prior Publication Data

US 2023/0270350 A1 Aug. 31, 2023

Related U.S. Application Data

(60) Provisional application No. 63/058,775, filed on Jul. 30, 2020.

(51) Int. Cl.
*A61B 5/08* (2006.01)
*A61B 5/00* (2006.01)
*G16H 50/20* (2018.01)

(52) U.S. Cl.
CPC .............. *A61B 5/08* (2013.01); *A61B 5/0022* (2013.01); *G16H 50/20* (2018.01)

(58) Field of Classification Search
CPC ....... A61B 5/08; A61B 5/0022; A61B 5/0826; A61B 5/361; G16H 50/20; G16H 20/40
See application file for complete search history.

(56) References Cited

U.S. PATENT DOCUMENTS 5,245,995 A 9/1993 Sullivan et al.
6,502,572 B1 1/2003 Berthon-Jones et al.
(Continued)

FOREIGN PATENT DOCUMENTS

WO 2008/138040 A1 11/2008
WO WO-2013052318 A1 * 4/2013 ......... G01N 35/1065
(Continued)

OTHER PUBLICATIONS

Ayappa et al., "Non-Invasive Detection of Respiratory Effort-Related Arousals (RERAs) by a Nasal Cannula/Pressure Transducer System", NYU School of Medicine; published in Sleep, vol. 23, No. 6, 2000, pp. 763-771.
(Continued)

*Primary Examiner* — Eric F Winakur
*Assistant Examiner* — Sienna C Pyle
(74) *Attorney, Agent, or Firm* — Nixon Peabody LLP

(57) ABSTRACT

Methods and systems determine health condition(s) from health data of a user of a respiratory system or operational conditions of a respiratory system. The health data or operational data are collected by processing device(s) local to the user. The method and system include analyzing the collected data to make an initial determination of potential health condition(s) associated with the user, or potential operational fault conditions of the respiratory system. In response to determining potential condition(s), a command is transmitted for receipt by a remote server. The command is to provide health assessment module(s) including instructions for analyzing the health data, or operational fault
(Continued)

assessment modules including instructions for analyzing the operational data, to further assess the initially determined potential condition(s). Health assessment module(s) or operational fault assessment module(s) are received on the processing device(s), which are updated to store the assessment module(s) as executable instructions for analyzing the health data or the operational data to verify the initial determination.

21 Claims, 7 Drawing Sheets

(56) References Cited

U.S. PATENT DOCUMENTS

| | | | | |
|---|---|---|---|---|
| 9,358,353 | B2 | 6/2016 | Armitstead et al. | |
| 10,492,720 | B2 | 12/2019 | Phillips et al. | |
| 10,549,053 | B2 | 2/2020 | Armitstead et al. | |
| 10,660,563 | B2 | 5/2020 | McDarby et al. | |
| 11,006,890 | B2 * | 5/2021 | Osorio | A61B 5/0205 |
| 2003/0187688 | A1 * | 10/2003 | Fey | G16H 10/60 705/2 |
| 2010/0312577 | A1 * | 12/2010 | Goodnow | G06F 13/4282 705/2 |
| 2017/0311879 | A1 | 11/2017 | Armitstead et al. | |
| 2017/0372600 | A1 * | 12/2017 | Palin | H04W 4/80 |
| 2019/0019581 | A1 * | 1/2019 | Vaughan | G16H 50/70 |
| 2020/0197640 | A1 | 6/2020 | Armitstead et al. | |
| 2020/0337634 | A1 | 10/2020 | McDarby et al. | |
| 2020/0383580 | A1 | 12/2020 | Shouldice et al. | |
| 2021/0150873 | A1 | 5/2021 | Shouldice et al. | |

FOREIGN PATENT DOCUMENTS

| | | | |
|---|---|---|---|
| WO | 2013/177621 | A1 | 12/2013 |
| WO | 2014/047310 | A1 | 3/2014 |
| WO | 2016/061629 | A1 | 4/2016 |
| WO | 2017/132726 | A1 | 8/2017 |
| WO | 2018/050913 | A1 | 3/2018 |
| WO | 2019/122413 | A1 | 6/2019 |
| WO | 2019/122414 | A1 | 6/2019 |
| WO | 2020/104465 | A2 | 5/2020 |

OTHER PUBLICATIONS

International Search Report in International Patent Application No. PCT/IB2021/056885 mailed Nov. 1, 2022 (5 pp.).

Written Opinion in International Patent Application No. PCT/IB2021/056885 mailed Nov. 1, 2022 (10 pp.).

* cited by examiner

SYSTEMS AND METHODS FOR DETERMINING A HEALTH CONDITION ON A DEVICE LOCAL TO A RESPIRATORY SYSTEM USER

CROSS-REFERENCE TO RELATED APPLICATIONS

This application is a U.S. National Stage of International Application No. PCT/IB2021/056885, filed on Jul. 28, 2021, which claims priority to, and the benefit of, U.S. Provisional Patent Application No. 63/058,775, filed on Jul. 30, 2020, the disclosure of each of which is hereby incorporated by reference herein in its entirety.

TECHNICAL FIELD

The present disclosure relates generally to systems and methods for determining health conditions of a user of a respiratory system, and more particularly, to systems and methods for determining health conditions of the user from health data being collected, stored, and analyzed on a device local to the user.

BACKGROUND

Many individuals suffer from sleep-related and/or respiratory disorders such as, for example, Periodic Limb Movement Disorder (PLMD), Restless Leg Syndrome (RLS), Sleep-Disordered Breathing (SDB) such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hypertension, diabetes, stroke, insomnia, and chest wall disorders.

Many of these sleep-related disorders can be treated via the use of respiratory therapy systems that supply pressurized air to the user's airway at night and collect various data about the user and system operations. A user may be concerned with the privacy of any collected personal data, including what happens to their health data. Some users may elect not to begin using a respiratory therapy system or discontinue use absent some reassurance that their data will remain private or a demonstration of the benefits of using a respiratory therapy system. The present disclosure is directed to solving these and other problems.

SUMMARY

According to some implementations of the present disclosure, method for determining one or more health conditions from health data of a user of a respiratory system includes analyzing health data being collected by and stored in a memory of one or more processing devices local to the user. The method includes analyzing the collected health data of the user to make an initial determination of one or more potential health conditions associated with the user of the respiratory system. In response to determining one or more potential health conditions associated with the user, the method includes transmitting for receipt by a remote server a command to provide one or more health assessment modules including instructions for analyzing the health data to further assess the initially determined one or more identified potential health conditions. In response to the one or more health assessment modules being provided by the remote server, the one or more health assessment modules are received on the one or more processing devices local to the user. The one or more processing devices local to the user are updated to store the one or more health assessment modules as executable instructions. One or more of the received health assessment modules are executed to analyze the health data to verify the initial determination of the user having one or more potential health conditions.

According to some implementations, a system comprises a control system including one or more processors and a memory having stored thereon machine readable instructions. The control system is coupled to the memory. The method for determining one or more health conditions from health data of a user of a respiratory system is implemented when the machine executable instructions in the memory are executed by at least one of the one or more processors of the control system.

According to some implementations, a system for determining one or more health conditions from health data of a user of a respiratory system includes a control system configured to implement a method. The method includes analyzing health data of a user collected by a processing device local to the user to make an initial determination of one or more potential health conditions associated with the user of the respiratory system. In response to determining one or more potential health conditions associated with the user, the method includes transmitting for receipt by a remote server a command to provide one or more health assessment modules including instructions for analyzing the health data to further assess the initially determined one or more identified potential health conditions. In response to the one or more health assessment modules being provided by the remote server, the one or more health assessment modules are received on the processing device local to the user. The processing device local to the user is updated to store the one or more health assessment modules as executable instructions. One or more of the received health assessment modules are executed to analyze the health data to verify the initial determination of the user having one or more potential health conditions.

According to some implementations, a computer program product comprising instructions which, when executed by a computer, cause the computer to carry out the method of determining one or more health conditions from health data of a user of a respiratory system. The method includes analyzing health data being collected by and stored in a memory of one or more processing devices local to the user to make an initial determination of one or more potential health conditions associated with the user of the respiratory system. In response to determining one or more potential health conditions associated with the user, the method includes transmitting for receipt by a remote server a command to provide one or more health assessment modules including instructions for analyzing the health data to further assess the initially determined one or more identified potential health conditions. In response to the one or more health assessment modules being provided by the remote server, the one or more health assessment modules are received on the one or more processing devices local to the user. The one or more processing devices local to the user are updated to store the one or more health assessment modules as executable instructions. One or more of the received health assessment modules are executed to analyze the health data to verify the initial determination of the user having one or more potential health conditions. According to some implementations, the computer program product is a non-transitory computer readable medium.

According to some implementations of the present disclosure, a method for determining one or more operational fault conditions from operational data of a respiratory system includes analyzing operational data being collected by and stored in a memory of one or more processing devices local to the user of the respiratory system. The method includes analyzing operational data for a respiratory system to make an initial determination of one or more potential operational fault conditions associated with the respiratory system. The operational data is collected by one or more processing devices local to the user. In response to determining one or more potential operational fault conditions associated with the respiratory system, the method includes transmitting for receipt by a remote server a command to provide one or more operational fault assessment modules including instructions for analyzing the operational data to further assess the initially determined one or more identified potential operational fault conditions. In response to the one or more operational fault assessment modules being provided by the remote server, the one or more operational fault assessment modules are received on the one or more processing devices local to the user. The one or more processing devices local to the user are updated to store the one or more operational fault assessment modules as executable instructions. One or more of the received operational fault assessment modules are executed to analyze the operational data to verify the initial determination of the respiratory system having one or more potential operational fault conditions.

According to some implementations, a system comprises a control system including one or more processors and a memory having stored thereon machine readable instructions. The control system is coupled to the memory. The method for determining one or more operational fault conditions from operational data of a respiratory system is implemented when the machine executable instructions in the memory are executed by at least one of the one or more processors of the control system.

According to some implementations, a system for determining one or more operational fault conditions from operational data of a respiratory system includes a control system configured to implement a method. The method includes analyzing operational data for a respiratory system to make an initial determination of one or more potential operational fault conditions associated with the respiratory system. The operational data is collected by one or more processing devices local to the user. In response to determining one or more potential operational fault conditions associated with the respiratory system, the method includes transmitting for receipt by a remote server a command to provide one or more operational fault assessment modules including instructions for analyzing the operational data to further assess the initially determined one or more identified potential operational fault conditions. In response to the one or more operational fault assessment modules being provided by the remote server, the one or more operational fault assessment modules are received on the one or more processing devices local to the user. The one or more processing devices local to the user are updated to store the one or more operational fault assessment modules as executable instructions. One or more of the received operational fault assessment modules are executed to analyze the operational data to verify the initial determination of the respiratory system having one or more potential operational fault conditions.

According to some implementations, a computer program product comprising instructions which, when executed by a computer, cause the computer to carry out the method of determining one or more operational fault conditions from operational data of respiratory system. The method includes analyzing operational being collected by and stored in a memory of one or more processing devices local to the user to make an initial determination of one or more potential operational fault conditions associated with the respiratory system. In response to determining one or more potential operational fault conditions associated with the respiratory system, the method includes transmitting for receipt by a remote server a command to provide one or more operational fault modules including instructions for analyzing the operational data to further assess the initially determined one or more identified potential operational fault conditions. In response to the one or more operational fault assessment modules being provided by the remote server, the one or more operational fault assessment modules are received on the one or more processing devices local to the user. The one or more processing devices local to the user are updated to store the one or more operational fault assessment modules as executable instructions. One or more of the received operational fault assessment modules are executed to analyze the operational data to verify the initial determination of the user having one or more potential operational fault conditions. According to some implementations, the computer program product is a non-transitory computer readable medium.

The above summary is not intended to represent each implementation or every aspect of the present disclosure. Additional features and benefits of the present disclosure are apparent from the detailed description and figures set forth below.

Figure 1A:
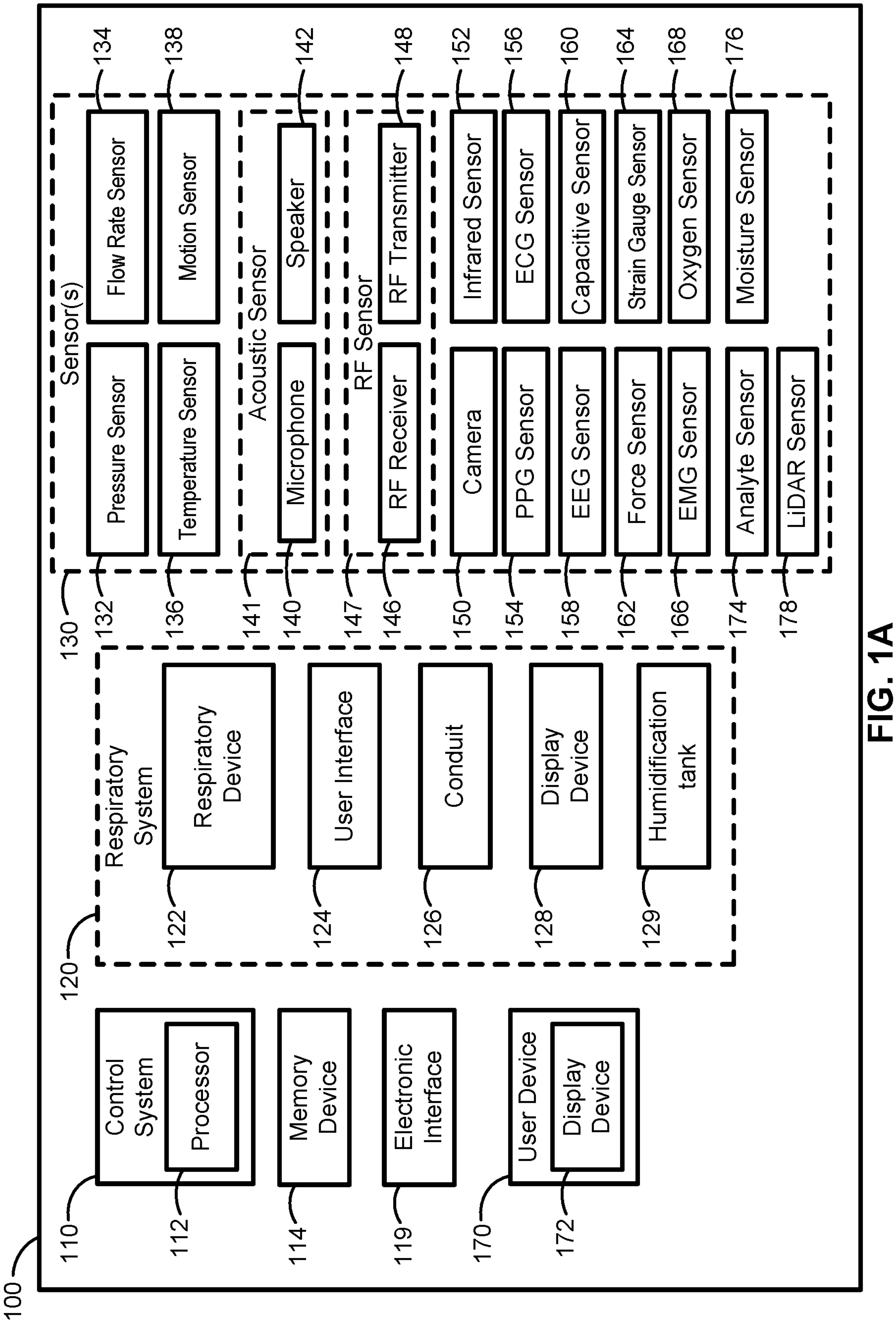
FIGS. 1A and 1B are functional block diagrams of system configurations, according to some implementations of the present disclosure.

While the present disclosure is susceptible to various modifications and alternative forms, specific implementations and embodiments thereof have been shown by way of example in the drawings and will herein be described in detail. It should be understood, however, that it is not intended to limit the present disclosure to the particular forms disclosed, but on the contrary, the present disclosure is to cover all modifications, equivalents, and alternatives falling within the spirit and scope of the present disclosure as defined by the appended claims.

DETAILED DESCRIPTION

Many individuals suffer from sleep-related and/or respiratory-related disorders such as, for example, Periodic Limb Movement Disorder (PLMD), Restless Leg Syndrome (RLS), Sleep-Disordered Breathing (SDB) such as Obstructive Sleep Apnea (OSA), Central Sleep Apnea (CSA), and other types of apneas such as mixed apneas and hypopneas, Respiratory Effort Related Arousal (RERA), Cheyne-Stokes Respiration (CSR), respiratory insufficiency, Obesity Hyperventilation Syndrome (OHS), Chronic Obstructive Pulmonary Disease (COPD), Neuromuscular Disease (NMD), rapid eye movement (REM) behavior disorder (also referred to as RBD), dream enactment behavior (DEB), hyper tension, diabetes, stroke, insomnia, and chest wall disorders.

Obstructive Sleep Apnea (OSA) is a form of Sleep Disordered Breathing (SDB), and is characterized by events including occlusion or obstruction of the upper air passage during sleep resulting from a combination of an abnormally small upper airway and the normal loss of muscle tone in the region of the tongue, soft palate and posterior oropharyngeal wall.

Central Sleep Apnea (CSA) is another form of SDB that results when the brain temporarily stops sending signals to the muscles that control breathing. More generally, an apnea generally refers to the cessation of breathing caused by blockage of the air or the stopping of the breathing function. Typically, the individual will stop breathing for between about 15 seconds and about 30 seconds during an obstructive sleep apnea event. Mixed sleep apnea is another form of SDB that is a combination of OSA and CSA.

Other types of apneas include hypopnea, hyperpnea, and hypercapnia. Hypopnea is generally characterized by slow or shallow breathing caused by a narrowed airway, as opposed to a blocked airway. Hyperpnea is generally characterized by an increased depth and/or rate of breathing. Hypercapnia is generally characterized by elevated or excessive carbon dioxide in the bloodstream, typically caused by inadequate respiration.

A Respiratory Effort Related Arousal (RERA) event is typically characterized by an increased respiratory effort for 10 seconds or longer leading to arousal from sleep and which does not fulfill the criteria for an apnea or hypopnea event. In 1999, the AASM Task Force defined RERAs as "a sequence of breaths characterized by increasing respiratory effort leading to an arousal from sleep, but which does not meet criteria for an apnea or hypopnea. These events must fulfil both of the following criteria: 1. pattern of progressively more negative esophageal pressure, terminated by a sudden change in pressure to a less negative level and an arousal; 2. the event lasts 10 seconds or longer. In 2000, the study "Non-Invasive Detection of Respiratory Effort-Related Arousals (RERAs) by a Nasal Cannula/Pressure Transducer System" done at NYU School of Medicine and published in Sleep, vol. 23, No. 6, pp. 763-771, demonstrated that a Nasal Cannula/Pressure Transducer System was adequate and reliable in the detection of RERAs. A RERA detector may be based on a real flow signal derived from a respiratory therapy (e.g., PAP) device. For example, a flow limitation measure may be determined based on a flow signal. A measure of arousal may then be derived as a function of the flow limitation measure and a measure of sudden increase in ventilation. One such method is described in WO 2008/138040, U.S. Pat. Nos. 9,358,353, 10,549,053, and US 2020/0197640, each of which are hereby incorporated herein by reference in their entirety.

Cheyne-Stokes Respiration (CSR) is another form of SDB. CSR is a disorder of a patient's respiratory controller in which there are rhythmic alternating periods of waxing and waning ventilation known as CSR cycles. CSR is characterized by repetitive de-oxygenation and re-oxygenation of the arterial blood.

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common, such as increased resistance to air movement, extended expiratory phase of respiration, and loss of the normal elasticity of the lung.

Neuromuscular Disease (NMD) encompasses many diseases and ailments that impair the functioning of the muscles either directly via intrinsic muscle pathology, or indirectly via nerve pathology. Chest wall disorders are a group of thoracic deformities that result in inefficient coupling between the respiratory muscles and the thoracic cage.

These and other disorders are characterized by particular events (e.g., snoring, an apnea, a hypopnea, a restless leg, a sleeping disorder, choking, an increased heart rate, labored breathing, an asthma attack, an epileptic episode, a seizure, or any combination thereof) that occur when the individual is sleeping.

The Apnea-Hypopnea Index (AHI) is an index used to indicate the severity of sleep apnea during a sleep session. The AHI is calculated by dividing the number of apnea and/or hypopnea events experienced by the user during the sleep session by the total number of hours of sleep in the sleep session. The event can be, for example, a pause in breathing that lasts for at least 10 seconds. An AHI that is less than 5 is considered normal. An AHI that is greater than or equal to 5, but less than 15 is considered indicative of mild sleep apnea. An AHI that is greater than or equal to 15, but less than 30 is considered indicative of moderate sleep apnea. An AHI that is greater than or equal to 30 is considered indicative of severe sleep apnea. In children, an AHI that is greater than 1 is considered abnormal. Sleep apnea can be considered "controlled" when the AHI is normal, or when the AHI is normal or mild. The AHI can also be used in combination with oxygen desaturation levels to indicate the severity of Obstructive Sleep Apnea.

Figure 1B:
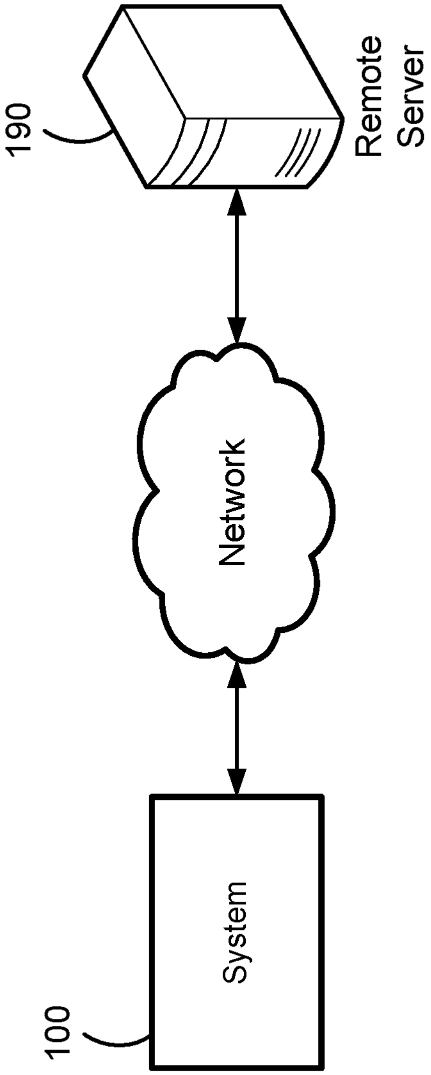

Referring to FIGS. 1A and 1B, functional block diagrams are depicted of configurations for a system 100, according to some implementations of the present disclosure. The system 100 is for supplying pressurized air to a user's airway during a sleep session using a respiratory therapy system, and for modifying the pressure settings of the respiratory therapy system. The system 100 includes a control system 110, a memory device 114, an electronic interface 119, one or more sensors 130, and one or more user devices 170. In some implementations, the system 100 further optionally includes a respiratory system 120. In some implementations, the system 100 is optionally connected via a computer network to a remote server system 190 (see, for example, FIG. 1B) allowing the transmission of data or instructions to the remote server 190 and the receipt of an assessment module therefrom, such as a health assessment module.

The control system 110 includes one or more processors 112 (hereinafter, processor 112). The control system 110 is generally used to control (e.g., actuate) the various components of the system 100 and/or analyze data obtained and/or generated by the components of the system 100. It is contemplated that in some implementations, health data is collected for a user of the system 100 where the collected data is stored and analyzed locally (e.g., on a respiratory device 122, user device 172, memory device 114, control system 110, and/or processor 112 local to the user) for making a determination of potential health condition(s) for the user associated with the collected data. The processor 112 can be a general or special purpose processor or microprocessor. While one processor 112 is shown in FIG. 1A, the control system 110 can include any suitable number of processors (e.g., one processor, two processors, five processors, ten processors, etc.) that can be in a single housing, or located remotely from each other. The control system 110 can be coupled to and/or positioned within, for example, a housing of the user device 170, and/or within a housing of one or more of the sensors 130. The control system 110 can be centralized (within one such housing) or decentralized (within two or more of such housings, which are physically distinct). In such implementations including two or more housings containing the control system 110, such housings can be located proximately and/or remotely from each other.

In some implementations, the control system 110 (or any other control system) or a portion of the control system 110 such as the processor 112 (or any other processor(s) or portion(s) of any other control system), can be used to carry out one or more steps of any of the methods described and/or claimed herein.

The memory device 114 stores machine-readable instructions that are executable by the processor 112 of the control system 110. The memory device 114 can be any suitable computer readable storage device or media, such as, for example, a random or serial access memory device, a hard drive, a solid state drive, a flash memory device, etc. While one memory device 114 is shown in FIG. 1A, the system 100 can include any suitable number of memory devices 114 (e.g., one memory device, two memory devices, five memory devices, ten memory devices, etc.). The memory device 114 can be coupled to and/or positioned within a housing of the respiratory device 122, within a housing of the user device 170, within a housing of one or more of the sensors 130, or any combination thereof. Like the control system 110, the memory device 114 can be centralized (within one such housing) or decentralized (within two or more of such housings, which are physically distinct).

In some implementations, the memory device 114 (FIG. 1A) stores a user profile associated with the user. The user profile can include, for example, health related data including demographic information associated with the user, biometric information associated with the user, medical information associated with the user, self-reported user feedback, sleep parameters associated with the user (e.g., sleep-related parameters recorded from one or more earlier sleep sessions), or any combination thereof. The demographic information can include, for example, information indicative of an age of the user, a gender of the user, a race of the user, a family medical history (such as a family history of insomnia or sleep apnea), an employment status of the user, an educational status of the user, a socioeconomic status of the user, or any combination thereof. The medical information can include, for example, information indicative of one or more current or historical medical conditions associated with the user, medication usage by the user, or both. The medical information data can further include, for example, an Epworth Sleepiness Score (ESS), a multiple sleep latency test (MSLT) result or score and/or a Pittsburgh Sleep Quality Index (PSQI) score or value. The self-reported user feedback can include, for example, information indicative of a self-reported subjective sleep score (e.g., poor, average, excellent), a self-reported subjective stress level of the user, a self-reported subjective fatigue level of the user, a self-reported subjective health status of the user, a recent life event experienced by the user, or any combination thereof.

The electronic interface 119 is configured to receive data (e.g., physiological data and/or acoustic data) from the one or more sensors 130 such that the data can be stored in the memory device 114 and/or analyzed by the processor 112 of the control system 110. The electronic interface 119 can communicate with the one or more sensors 130 using a wired connection or a wireless connection (e.g., using a RF communication protocol, a WiFi communication protocol, a Bluetooth communication protocol, an IR communication protocol, over a cellular network, over any other optical communication protocol, etc.). The electronic interface 119 can include an antenna, a receiver (e.g., a RF receiver), a transmitter (e.g., a RF transmitter), a transceiver, or any combination thereof. The electronic interface 119 can also include one more processors and/or one more memory devices that are the same as, or similar to, the processor 112 and the memory device 114 described herein. In some implementations, the electronic interface 119 is coupled to or integrated in the user device 170. In other implementations, the electronic interface 119 is coupled to or integrated (e.g., in a housing) with the control system 110 and/or the memory device 114.

As noted above, in some implementations, the system 100 optionally includes a respiratory system 120 (also referred to as a respiratory therapy system or a respiratory pressure therapy system). The respiratory system 120 can include a respiratory device 122 (also referred to as respiratory therapy device or a respiratory pressure therapy device), a user interface 124 (also referred to as a mask or a patient interface), a conduit 126 (also referred to as a tube or an air circuit), a display device 128, a humidification tank 129, or any combination thereof. In some implementations, the control system 110, the memory device 114, the display device 128, one or more of the sensors 130, and the humidification tank 129 are part of the respiratory device 122. Respiratory pressure therapy refers to the application of a supply of air to an entrance to a user's airways at a controlled target pressure that is nominally positive with respect to atmosphere throughout the user's breathing cycle (e.g., in contrast to negative pressure therapies such as the tank ventilator or cuirass). The respiratory system 120 is generally used to treat individuals suffering from one or more sleep-related respiratory disorders (e.g., obstructive sleep apnea, central sleep apnea, or mixed sleep apnea), other respiratory disorders such as COPD, or other disorders leading to respiratory insufficiency, that may manifest either during sleep or wakefulness.

The respiratory device 122 is generally used to generate pressurized air that is delivered to a user (e.g., using one or more motors that drive one or more compressors). In some implementations, the respiratory device 122 generates continuous constant air pressure that is delivered to the user. In other implementations, the respiratory device 122 generates two or more predetermined pressures (e.g., a first predetermined air pressure and a second predetermined air pressure). In still other implementations, the respiratory device 122 is configured to generate a variety of different air pressures within a predetermined range. For example, the respiratory device 122 can deliver at least about 6 cm $H_2O$, at least about 10 cm $H_2O$, at least about 20 cm $H_2O$, between about 6 cm $H_2O$ and about 10 cm $H_2O$, between about 7 cm $H_2O$ and about 12 cm $H_2O$, etc. The respiratory device 122 can also deliver pressurized air at a predetermined flow rate between, for example, about −20 L/min and about 150 L/min, while maintaining a positive pressure (relative to the ambient pressure). In some implementations, the control system 110, the memory device 114, the electronic interface 119, or any combination thereof can be coupled to and/or positioned within a housing of the respiratory device 122.

The user interface 124 engages a portion of the user's face and delivers pressurized air from the respiratory device 122 to the user's airway to aid in preventing the airway from narrowing and/or collapsing during sleep. This may also increase the user's oxygen intake during sleep. Depending upon the therapy to be applied, the user interface 124 may form a seal, for example, with a region or portion of the user's face, to facilitate the delivery of gas at a pressure at sufficient variance with ambient pressure to effect therapy, for example, at a positive pressure of about 10 cm $H_2O$ relative to ambient pressure. For other forms of therapy, such as the delivery of oxygen, the user interface may not include a seal sufficient to facilitate delivery to the airways of a supply of gas at a positive pressure of about 10 cm $H_2O$.

Figure 2:
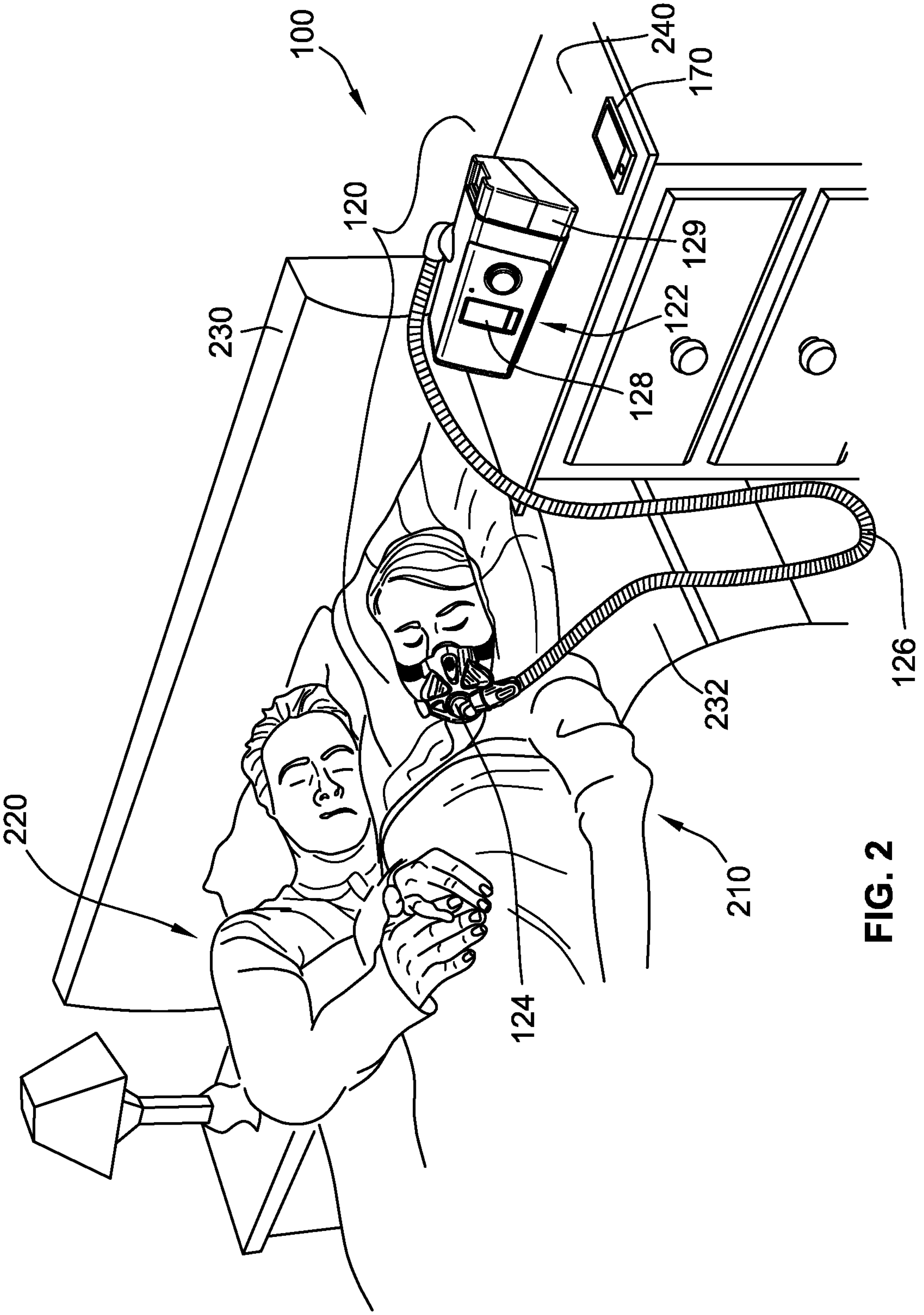
FIG. 2 is a perspective view of at least a portion of the system of FIG. 1A, a user, and a bed partner, according to some implementations of the present disclosure.

In some implementations, the user interface 124 is, or includes, a facial mask that covers the nose and mouth of the user (as shown, for example, in FIG. 2). Alternatively, the user interface 124 is, or includes, a nasal mask that provides air to the nose of the user or a nasal pillow mask that delivers air directly to the nostrils of the user. The user interface 124 can include a strap assembly that has a plurality of straps (e.g., including hook and loop fasteners) for positioning and/or stabilizing the user interface 124 on a desired location of the user (e.g., the face), and a conformal cushion (e.g., silicone, plastic, foam, etc.) that aids in providing an air-tight seal between the user interface 124 and the user. In some implementations, the user interface 124 may include a connector and one or more vents. The one or more vents can be used to permit the escape of carbon dioxide and other gases exhaled by the user. In other implementations, the user interface 124 includes a mouthpiece (e.g., a night guard mouthpiece molded to conform to the user's teeth, a mandibular repositioning device, etc.). In some implementations, the connector is distinct from, but couplable to, the user interface 124 (and/or conduit 126). The connector is configured to connect and fluidly couple the user interface 124 to the conduit 126.

The conduit 126 (also referred to as an air circuit or tube) allows the flow of air between two components of a respiratory system 120, such as the respiratory device 122 and the user interface 124. In some implementations, there can be separate limbs of the conduit for inhalation and exhalation. In other implementations, a single limb conduit is used for both inhalation and exhalation. Generally, the respiratory system 120 forms an air pathway that extends between a motor of the respiratory device 122 and the user and/or the user's airway. Thus, the air pathway generally includes at least a motor of the respiratory device 122, the user interface 124, and the conduit 126.

One or more of the respiratory device 122, the user interface 124, the conduit 126, the display device 128, and the humidification tank 129 can contain one or more sensors (e.g., a pressure sensor, a flow rate sensor, or more generally any of the other sensors 130 described herein). These one or more sensors can be used, for example, to measure the air pressure and/or flow rate of pressurized air supplied by the respiratory device 122.

The display device 128 is generally used to display image(s) including still images, video images, or both and/or information regarding the respiratory device 122 and/or other components of the respiratory system 120. For example, the display device 128 can provide information regarding the status of the respiratory device 122 (e.g., whether the respiratory device 122 is on/off, the pressure of the air being delivered by the respiratory device 122, the temperature of the air being delivered by the respiratory device 122, etc.), the current date/time, personal information for the user 210, and/or other information (e.g., a sleep score or a therapy score, such as, a myAir™ score, described in WO 2016/061629 and US 2017/0311879, each of which are hereby incorporated by reference herein in their entirety), etc. In some implementations, the display device 128 acts as a human-machine interface (HMI) that includes a graphic user interface (GUI) configured to display the image(s) as an input interface. The display device 128 can be an LED display, an OLED display, an LCD display, or the like. The input interface can be, for example, a touchscreen or touch-sensitive substrate, a mouse, a keyboard, or any sensor system configured to sense inputs made by a human user interacting with the respiratory device 122.

The humidification tank 129 is coupled to or integrated in the respiratory device 122 and includes a reservoir of water that can be used to humidify the pressurized air delivered from the respiratory device 122. The respiratory device 122 can include a heater to heat the water in the humidification tank 129 in order to humidify the pressurized air provided to the user. Additionally, in some implementations, the conduit 126 can also include a heating element (e.g., coupled to and/or imbedded in the conduit 126) that heats the pressurized air delivered to the user. In some implementations, the respiratory therapy device 122 or the conduit 126 can include a waterless humidifier. The waterless humidifier can incorporate sensors that interface with other sensor positioned elsewhere in the system 100.

The respiratory system 120 can be used, for example, as a ventilator or a positive airway pressure (PAP) system, such as a continuous positive airway pressure (CPAP) system, an automatic positive airway pressure system (APAP), a bi-level or variable positive airway pressure system (BPAP or VPAP), or any combination thereof. The CPAP system delivers a predetermined air pressure (e.g., determined by a sleep physician) to the user. The APAP system automatically varies the air pressure delivered to the user at least in part based on, for example, respiration data associated with the user. The BPAP or VPAP system is configured to deliver a first predetermined pressure (e.g., an inspiratory positive airway pressure or IPAP) and a second predetermined pressure (e.g., an expiratory positive airway pressure or EPAP) that is lower than the first predetermined pressure. A ventilator, such as the ResMed Elisée™ 150 ventilator and ResMed VS III™ ventilator, may provide support for invasive and non-invasive dependent ventilation suitable for adult or pediatric patients for treating a number of conditions, and in some implementations includes providing volumetric and barometric ventilation modes with a single or double limb circuit.

Referring to FIG. 2, a portion of the system 100 (see FIGS. 1A and 1B), according to some implementations, is illustrated. A user 210 of the respiratory system 120 and a bed partner 220 are located in a bed 230 and are laying on a mattress 232. The user interface 124 (e.g., a full facial mask) can be worn by the user 210 during a sleep session. The user interface 124 is fluidly coupled and/or connected to the respiratory device 122 via the conduit 126. In turn, the respiratory device 122 delivers pressurized air to the user 210 via the conduit 126 and the user interface 124 to increase the air pressure in the throat of the user 210 to aid in preventing the airway from closing and/or narrowing during sleep. The respiratory device 122 can include the display device 128, which can allow the user to interact with the respiratory device 122. The respiratory device 122 can also include the humidification tank 129, which stores the water used to humidify the pressurized air. The respiratory device 122 can be positioned on a nightstand 240 that is directly adjacent to the bed 230 as shown in FIG. 2, or more generally, on any surface or structure that is generally adjacent to the bed 230 and/or the user 210.

Referring back to FIG. 1A, the one or more sensors 130 of the system 100 include a pressure sensor 132, a flow rate sensor 134, temperature sensor 136, a motion sensor 138, a microphone 140, a speaker 142, a radio-frequency (RF) receiver 146, a RF transmitter 148, a camera 150, an infrared (IR) sensor 152, a photoplethysmogram (PPG) sensor 154, an electrocardiogram (ECG) sensor 156, an electroencephalography (EEG) sensor 158, a capacitive sensor 160, a force sensor 162, a strain gauge sensor 164, an electromyography (EMG) sensor 166, an oxygen sensor 168, an analyte sensor 174, a moisture sensor 176, a light detection and ranging (LiDAR) sensor 178, or any combination thereof. Generally, each of the one or sensors 130 are configured to output or generated health sensor data that is received and stored in the memory device 114 or one or more other memory devices. The sensors 130 can also include, an electrooculography (EOG) sensor, a peripheral oxygen saturation (SpO2) sensor, a galvanic skin response (GSR) sensor, a carbon dioxide (CO2) sensor, or any combination thereof.

While the one or more sensors 130 are shown and described as including each of the pressure sensor 132, the flow rate sensor 134, the temperature sensor 136, the motion sensor 138, the microphone 140, the speaker 142, the RF receiver 146, the RF transmitter 148, the camera 150, the IR sensor 152, the PPG sensor 154, the ECG sensor 156, the EEG sensor 158, the capacitive sensor 160, the force sensor 162, the strain gauge sensor 164, the EMG sensor 166, the oxygen sensor 168, the analyte sensor 174, the moisture sensor 176, and the LiDAR sensor 178, more generally, the one or more sensors 130 can include any combination and any number of each of the sensors described and/or shown herein.

The one or more sensors 130 can be used to generate health data. For example, the one or more sensors can be used to generate physiological data, acoustic data, operational data of the respiratory system, duration of respiratory therapy data, user interface data, facial feature data, or any combinations thereof, that is associated with a user of the respiratory system 120 (such as the user 210 of FIG. 2), the respiratory system 120, both the user and the respiratory system 120, or other entities, objects, activities, etc. Physiological data generated by one or more of the sensors 130 can be used by the control system 110 to determine a sleep-wake signal associated with the user during a sleep session and one or more sleep-related parameters. The sleep-wake signal can be indicative of one or more sleep stages (sometimes referred to as sleep states), including sleep, wakefulness, relaxed wakefulness, micro-awakenings, or distinct sleep stages such as rapid eye movement (REM) stage (which can include both a typical REM stage and an atypical REM stage), a first non-REM stage (often referred to as "N1"), a second non-REM stage (often referred to as "N2"), a third non-REM stage (often referred to as "N3"), or any combination thereof. Methods for determining sleep stages from physiological data generated by one or more of the sensors, such as sensors 130, are described in, for example, WO 2014/047310, U.S. Pat. Nos. 10,492,720, 10,660,563, US 2020/0337634, WO 2017/132726, WO 2019/122413, US 2021/0150873, WO 2019/122414, US 2020/0383580, each of which are hereby incorporated by reference herein in their entirety.

The sleep-wake signal can also be timestamped to indicate a time that the user enters the bed, a time that the user exits the bed, a time that the user attempts to fall asleep, etc. The sleep-wake signal can be measured by one or more of the sensors 130 during the sleep session at a predetermined sampling rate, such as, for example, one sample per second, one sample per 30 seconds, one sample per minute, etc. Examples of the one or more sleep-related parameters that can be determined for the user during the sleep session based at least in part on the sleep-wake signal include a total time in bed, a total sleep time, a total wake time, a sleep onset latency, a wake-after-sleep-onset parameter, a sleep efficiency, a fragmentation index, an amount of time to fall asleep, a consistency of breathing rate, a fall asleep time, a wake time, a rate of sleep disturbances, a number of movements, or any combination thereof. In some implementations, the system may also track apnea and hypopnea events and types across one or more sensors in order to understand the effective AHI for one or more sleep sessions (e.g., a user may be using a therapy device for only part of the sleep or in-bed session).

Physiological data and/or acoustic data generated by the one or more sensors 130 can also be used to determine a respiration signal associated with the user during a sleep session. The respiration signal is generally indicative of respiration or breathing of the user during the sleep session. The respiration signal can be indicative of, for example, a respiration rate, a respiration rate variability, an inspiration amplitude, an expiration amplitude, an inspiration-expiration ratio, amplitude ratio, an inspiration-expiration duration ratio, a number of events per hour, a pattern of events, pressure settings of the respiratory device 122, or any combination thereof. The event(s) can include snoring, apneas, central apneas, obstructive apneas, mixed apneas, hypopneas, RERAs, a flow limitation (e.g., an event that results in the absence of the increase in flow despite an elevation in negative intrathoracic pressure indicating increased effort), a mask leak (e.g., from the user interface 124), a restless leg, a sleeping disorder, choking, an increased heart rate, a heart rate variation, labored breathing, an asthma attack, an epileptic episode, a seizure, a fever, a cough, a sneeze, a snore, a gasp, the presence of an illness such as the common cold or the flu, an elevated stress level, etc. Events can be detected by any means known in the art such as described in, for example, U.S. Pat. Nos. 5,245,995, 6,502,572, WO 2018/050913, WO 2020/104465, each of which are incorporated by reference herein in their entirety.

The pressure sensor 132 outputs pressure data that can be stored in the memory device 114 and/or analyzed by the processor 112 of the control system 110. In some implementations, the pressure sensor 132 is an air pressure sensor (e.g., barometric pressure sensor) that generates sensor data indicative of the respiration (e.g., inhaling and/or exhaling) of the user of the respiratory system 120 and/or ambient pressure. In such implementations, the pressure sensor 132 can be coupled to or integrated in the respiratory device 122, the user interface 124, or the conduit 126. The pressure sensor 132 can be used to determine an air pressure in the respiratory device 122, an air pressure in the conduit 126, an air pressure in the user interface 124, or any combinations thereof. The pressure sensor 132 can be, for example, a capacitive sensor, an electromagnetic sensor, an inductive sensor, a resistive sensor, a piezoelectric sensor, a strain-gauge sensor, an optical sensor, a potentiometric sensor, or any combination thereof. In one example, the pressure sensor 132 can be used to determine a blood pressure of the user.

The flow rate sensor 134 outputs flow rate data that can be stored in the memory device 114 and/or analyzed by the processor 112 of the control system 110. In some implementations, the flow rate sensor 134 is used to determine an air flow rate from the respiratory device 122, an air flow rate through the conduit 126, an air flow rate through the user interface 124, or any combination thereof. In such implementations, the flow rate sensor 134 can be coupled to or integrated in the respiratory device 122, the user interface 124, or the conduit 126. The flow rate sensor 134 can be a mass flow rate sensor such as, for example, a rotary flow meter (e.g., Hall effect flow meters), a turbine flow meter, an orifice flow meter, an ultrasonic flow meter, a hot wire sensor, a vortex sensor, a membrane sensor, or any combination thereof.

The temperature sensor 136 outputs temperature data that can be stored in the memory device 114 and/or analyzed by the processor 112 of the control system 110. In some implementations, the temperature sensor 136 generates temperature data indicative of a core body temperature of the user, a skin temperature of the user, a temperature of the air flowing from the respiratory device 122 and/or through the conduit 126, a temperature in the user interface 124, an ambient temperature, or any combination thereof. The temperature sensor 136 can be, for example, a thermocouple sensor, a thermistor sensor, a silicon band gap temperature sensor or semiconductor-based sensor, a resistance temperature detector, or any combination thereof.

The motion sensor 138 outputs motion data that can be stored in the memory device 114 and/or analyzed by the processor 112 of the control system 110. The motion sensor 138 can be used to detect movement of the user during the sleep session, and/or detect movement of any of the components of the respiratory therapy system 120, such as the respiratory therapy device 122, the user interface 124, or the conduit 126. The motion sensor 138 can include one or more inertial sensors, such as accelerometers, gyroscopes, and magnetometers. The motion sensor 138 can be used to detect motion or acceleration associated with arterial pulses, such as pulses in or around the face of the user and proximal to the user interface 124, and configured to detect features of the pulse shape, speed, amplitude, or volume.

The microphone 140 outputs acoustic data that can be stored in the memory device 114 and/or analyzed by the processor 112 of the control system 110. The acoustic data generated by the microphone 140 is reproducible as one or more sound(s) during a sleep session (e.g., sounds from the user) to determine (e.g., using the control system 110) one or more sleep-related parameters, as described in further detail herein. The acoustic data from the microphone 140 can also be used to identify (e.g., using the control system 110) an event experienced by the user during the sleep session, as described in further detail herein. In other implementations, the acoustic data from the microphone 140 is representative of noise associated with the respiratory system 120. The microphone 140 can be coupled to or integrated in the respiratory system 120 (or the system 100) generally in any configuration. For example, the microphone 140 can be disposed inside the respiratory device 122, the user interface 124, the conduit 126, or other components. The microphone 140 can also be positioned adjacent to or coupled to the outside of the respiratory device 122, the outside of the user interface 124, the outside of the conduit 126, or outside of any other components. The microphone 140 could also be a component of the user device 170 (e.g., the microphone 140 is a microphone of a smart phone). The microphone 140 can be integrated into the user interface 124, the conduit 126, the respiratory device 122, or any combination thereof. In general, the microphone 140 can be located at any point within or adjacent to the air pathway of the respiratory system 120, which includes at least the motor of the respiratory device 122, the user interface 124, and the conduit 126. Thus, the air pathway can also be referred to as the acoustic pathway.

The speaker 142 outputs sound waves that are audible to the user. The speaker 142 can be used, for example, as an alarm clock or to play an alert or message to the user (e.g., in response to an event). In some implementations, the speaker 142 can be used to communicate the acoustic data generated by the microphone 140 to the user. The speaker 142 can be coupled to or integrated in the respiratory device 122, the user interface 124, the conduit 126, or the user device 170.

The microphone 140 and the speaker 142 can be used as separate devices. In some implementations, the microphone 140 and the speaker 142 can be combined into an acoustic sensor 141 (e.g., a SONAR sensor), as described in, for example, WO 2018/050913 and WO 2020/104465, each of which are hereby incorporated by reference herein in their entirety. In such implementations, the speaker 142 generates or emits sound waves at a predetermined interval and/or frequency, and the microphone 140 detects the reflections of the emitted sound waves from the speaker 142. The sound waves generated or emitted by the speaker 142 have a frequency that is not audible to the human ear (e.g., below 20 Hz or above around 18 kHz) so as not to disturb the sleep of the user or a bed partner of the user (such as bed partner 220 in FIG. 2). Based at least in part on the data from the microphone 140 and/or the speaker 142, the control system 110 can determine a location of the user and/or one or more of the sleep-related parameters described in herein, such as, for example, a respiration signal, a respiration rate, an inspiration amplitude, an expiration amplitude, an inspiration-expiration ratio, a number of events per hour, a pattern of events, a sleep stage, pressure settings of the respiratory device 122, or any combination thereof. In this context, a SONAR sensor may be understood to concern an active acoustic sensing, such as by generating/transmitting ultrasound or low frequency ultrasound sensing signals (e.g., in a frequency range of about 17-23 kHz, 18-22 kHz, or 17-18 kHz, for example), through the air. Such a system may be considered in relation to WO 2018/050913 and WO 2020/104465 mentioned above. In some implementations, the speaker 142 is a bone conduction speaker. In some implementations, the one or more sensors 130 include (i) a first microphone that is the same or similar to the microphone 140, and is integrated into the acoustic sensor 141 and (ii) a second microphone that is the same as or similar to the microphone 140, but is separate and distinct from the first microphone that is integrated into the acoustic sensor 141.

The RF transmitter 148 generates and/or emits radio waves having a predetermined frequency and/or a predetermined amplitude (e.g., within a high frequency band, within a low frequency band, long wave signals, short wave signals, etc.). The RF receiver 146 detects the reflections of the radio waves emitted from the RF transmitter 148, and this data can be analyzed by the control system 110 to determine a location of the user 210 (FIG. 2) and/or one or more of the sleep-related parameters described herein. A RF receiver (either the RF receiver 146 and the RF transmitter 148 or another RF pair) can also be used for wireless communication between the control system 110, the respiratory device 122, the one or more sensors 130, the user device 170, or any combination thereof. While the RF receiver 146 and RF transmitter 148 are shown as being separate and distinct elements in FIG. 1A, in some implementations, the RF receiver 146 and RF transmitter 148 are combined as a part of a RF sensor 147 (e.g., a RADAR sensor). In some such implementations, the RF sensor 147 includes a control circuit. The specific format of the RF communication can be WiFi, Bluetooth, etc.

In some implementations, the RF sensor 147 is a part of a mesh system. One example of a mesh system is a WiFi mesh system, which can include mesh nodes, mesh router(s), and mesh gateway(s), each of which can be mobile/movable or fixed. In such implementations, the WiFi mesh system includes a WiFi router and/or a WiFi controller and one or more satellites (e.g., access points), each of which include a RF sensor that the is the same as, or similar to, the RF sensor 147. The WiFi router and satellites continuously communicate with one another using WiFi signals. The WiFi mesh system can be used to generate motion data based at least in part on changes in the WiFi signals (e.g., differences in received signal strength) between the router and the satellite(s) due to an object or person moving partially obstructing the signals. The motion data can be indicative of motion, breathing, heart rate, gait, falls, behavior, etc., or any combination thereof.

The camera 150 outputs image data reproducible as one or more images (e.g., still images, video images, thermal images, or a combination thereof) that can be stored in the memory device 114. The image data from the camera 150 can be used by the control system 110 to determine one or more of the sleep-related parameters described herein. For example, the image data from the camera 150 can be used to identify a location of the user, to determine a time when the user enters the user's bed (such as bed 230 in FIG. 2), and to determine a time when the user exits the bed 230. The camera 150 can also be used to track eye movements, pupil dilation (if one or both of the user's eyes are open), blink rate, or any changes during REM sleep. The camera 150 can also be used to track the position of the user, which can impact the duration and/or severity of apneic episodes in users with positional obstructive sleep apnea.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can detect infrared light having a wavelength between about 700 nm and about 1 mm, for example, while the camera 150 can detect visible light having a wavelength between about 380 nm and about 740 nm.

The IR sensor 152 outputs infrared image data reproducible as one or more infrared images (e.g., still images, video images, or both) that can be stored in the memory device 114. The infrared data from the IR sensor 152 can be used to determine one or more sleep-related parameters during the sleep session, including a temperature of the user and/or movement of the user. The IR sensor 152 can also be used in conjunction with the camera 150 when measuring the presence, location, and/or movement of the user. The IR sensor 152 can also be used in conjunction with the camera 150 when measuring the presence, location, and/or movement of the user. The IR sensor 152 can detect infrared light having a wavelength between about 700 nm and about 1 mm, for example, while the camera 150 can detect visible light having a wavelength between about 380 nm and about 740 nm.

The PPG sensor 154 outputs physiological data associated with the user that can be used to determine one or more sleep-related parameters, such as, for example, a heart rate, a heart rate pattern, a heart rate variability, a cardiac cycle, respiration rate, an inspiration amplitude, an expiration amplitude, an inspiration-expiration ratio, estimated blood pressure parameter(s), or any combination thereof. The PPG sensor 154 can be worn by the user, embedded in clothing and/or fabric that is worn by the user, embedded in and/or coupled to the user interface 124 and/or its associated headgear (e.g., straps, etc.), etc. In some implementations, the PPG sensing can be performed from a distance, such as by processing changes in pixel or subpixel values such as color values and intensity as detected by video from a camera such as in a smartphone. Such PPG sensing may be made via of video of areas such as part of the face, and used to estimate heart rate, breathing rate, pulse transit time, hemoglobin levels, blood pressure and so forth. Such PPG may use visible and/or near infrared imagining, depending on lighting conditions.

The ECG sensor 156 outputs physiological data associated with electrical activity of the heart of the user. In some implementations, the ECG sensor 156 includes one or more electrodes that are positioned on or around a portion of the user during the sleep session. The physiological data from the ECG sensor 156 can be used, for example, to determine one or more of the sleep-related parameters described herein.

The EEG sensor 158 outputs physiological data associated with electrical activity of the brain of the user. In some implementations, the EEG sensor 158 includes one or more electrodes that are positioned on or around the scalp of the user 210 during the sleep session. The physiological data from the EEG sensor 158 can be used, for example, to determine a sleep stage of the user at any given time during the sleep session. In some implementations, the EEG sensor 158 can be integrated in the user interface 124 and/or the associated headgear (e.g., straps, etc.).

The capacitive sensor 160, the force sensor 162, and the strain gauge sensor 164 output data that can be stored in the memory device 114 and used by the control system 110 to determine one or more of the sleep-related parameters described herein. The EMG sensor 166 outputs physiological data associated with electrical activity produced by one or more muscles. The oxygen sensor 168 outputs oxygen data indicative of an oxygen concentration of gas (e.g., in the conduit 126 or at the user interface 124). The oxygen sensor 168 can be, for example, an ultrasonic oxygen sensor, an electrical oxygen sensor, a chemical oxygen sensor, an optical oxygen sensor, or any combination thereof. In some implementations, the one or more sensors 130 also include a galvanic skin response (GSR) sensor, a blood flow sensor, a respiration sensor, a pulse sensor, a sphygmomanometer sensor, an oximetry sensor, or any combination thereof.

The analyte sensor 174 can be used to detect the presence of an analyte in the exhaled breath of the user. The data output by the analyte sensor 174 can be stored in the memory device 114 and used by the control system 110 to determine the identity and concentration of any analytes in the user's breath. In some implementations, the analyte sensor 174 is positioned near a mouth of the user to detect analytes in breath exhaled from the user's mouth. For example, when the user interface 124 is a facial mask that covers the nose and mouth of the user, the analyte sensor 174 can be positioned within the facial mask to monitor the user's mouth breathing. In other implementations, such as when the user interface 124 is a nasal mask or a nasal pillow mask, the analyte sensor 174 can be positioned near the nose of the user to detect analytes in breath exhaled through the user's nose. In still other implementations, the analyte sensor 174 can be positioned near the user's mouth when the user interface 124 is a nasal mask or a nasal pillow mask. In this implementation, the analyte sensor 174 can be used to detect whether any air is inadvertently leaking from the user's mouth. In some implementations, the analyte sensor 174 is a volatile organic compound (VOC) sensor that can be used to detect carbon-based chemicals or compounds, such as carbon dioxide. In some implementations, the analyte sensor 174 can also be used to detect whether the user is breathing through their nose or mouth. For example, if the data output by an analyte sensor 174 positioned near the mouth of the user or within the facial mask (in implementations where the user interface 124 is a facial mask) detects the presence of an analyte, the control system 110 can use this data as an indication that the user is breathing through their mouth.

The moisture sensor 176 outputs data that can be stored in the memory device 114 and used by the control system 110. The moisture sensor 176 can be used to detect moisture in various areas surrounding the user (e.g., inside the conduit 126 or the user interface 124, near the user 210's face, near the connection between the conduit 126 and the user interface 124, near the connection between the conduit 126 and the respiratory device 122, etc.). Thus, in some implementations, the moisture sensor 176 can be coupled to or integrated into the user interface 124 or in the conduit 126 to monitor the humidity of the pressurized air from the respiratory device 122. In other implementations, the moisture sensor 176 is placed near any area where moisture levels need to be monitored. The moisture sensor 176 can also be used to monitor the humidity of the ambient environment surrounding the user, for example, the air inside the user's bedroom. The moisture sensor 176 can also be used to track the user's biometric response to environmental changes.

One or more LiDAR sensors 178 can be used for depth sensing. This type of optical sensor (e.g., laser sensor) can be used to detect objects and build three dimensional (3D) maps of the surroundings, such as of a living space. LiDAR can generally utilize a pulsed laser to make time of flight measurements. LiDAR is also referred to as 3D laser scanning. In an example of use of such a sensor, a fixed or mobile device (such as a smartphone) having a LiDAR sensor 178 can measure and map an area extending 5 meters or more away from the sensor. The LiDAR data can be fused with point cloud data estimated by an electromagnetic RADAR sensor, for example. The LiDAR sensor(s) 178 can also use artificial intelligence (AI) to automatically geofence RADAR systems by detecting and classifying features in a space that might cause issues for RADAR systems, such a glass windows (which can be highly reflective to RADAR). LiDAR can also be used to provide an estimate of the height of a person, as well as changes in height when the person sits down, or falls down, for example. LiDAR may be used to form a 3D mesh representation of an environment. In a further use, for solid surfaces through which radio waves pass (e.g., radio-translucent materials), the LiDAR may reflect off such surfaces, thus allowing a classification of different type of obstacles.

While shown separately in FIG. 1A, any combination of the one or more sensors 130 can be integrated in and/or coupled to any one or more of the components of the system 100, including the respiratory device 122, the user interface 124, the conduit 126, the humidification tank 129, the control system 110, the user device 170, or any combination thereof. For example, the acoustic sensor 141 and/or RF sensor 147 can be is integrated in and/or coupled to the user device 170. In such implementations, the user device 170 can be considered a secondary device that generates additional or secondary data for use by the system 100 (e.g., the control system 110) according to some aspects of the present disclosure. In some implementations, the pressure sensor 132 and/or the flow rate sensor 134 are integrated into and/or coupled to the respiratory device 122. In some implementations, at least one of the one or more sensors 130 is not coupled to the respiratory device 122, the control system 110, or the user device 170, and is positioned generally adjacent to the user during the sleep session (e.g., positioned on or in contact with a portion of the user, worn by the user, coupled to or positioned on the nightstand, coupled to the mattress, coupled to the ceiling, etc.). More generally, the one or more sensors 130 can be positioned at any suitable location relative to the user such that the one or more sensors 130 can generate physiological data associated with the user and/or the bed partner 220 during one or more sleep session.

The data from the one or more sensors 130 can be analyzed to determine one or more sleep-related parameters, which can include a respiration signal, a respiration rate, a respiration pattern, an inspiration amplitude, an expiration amplitude, an inspiration-expiration ratio, an occurrence of one or more events, a number of events per hour, a pattern of events, an average duration of events, a range of event durations, a ratio between the number of different events, a sleep stage, an apnea-hypopnea index (AHI), or any combination thereof. The one or more events can include snoring, apneas, central apneas, obstructive apneas, mixed apneas, hypopneas, an intentional user interface leak, an unintentional user interface leak, a mouth leak, a cough, a restless leg, a sleeping disorder, choking, an increased heart rate, labored breathing, an asthma attack, an epileptic episode, a seizure, increased blood pressure, hyperventilation, or any combination thereof. Many of these sleep-related parameters are physiological parameters, although some of the sleep-related parameters can be considered to be non-physiological parameters. Other types of physiological and non-physiological parameters can also be determined, either from the data from the one or more sensors 130, or from other types of data.

The user device 170 (FIG. 1A) includes a display device 172. The user device 170 can be, for example, a mobile device such as a smart phone, a tablet, a laptop, or the like. Alternatively, the user device 170 can be an external sensing system, a television (e.g., a smart television) or another smart home device (e.g., a smart speaker(s) such as Google Home, Amazon Echo, Alexa etc.). In some implementations, the user device 170 is a wearable device (e.g., a smart watch). The display device 172 is generally used to display image(s) including still images, video images, or both. In some implementations, the display device 172 acts as a human-machine interface (HMI) that includes a graphic user interface (GUI) configured to display the image(s) and an input interface. The display device 172 can be an LED display, an OLED display, an LCD display, or the like. The input interface can be, for example, a touchscreen or touch-sensitive substrate, a mouse, a keyboard, or any sensor system configured to sense inputs made by a human user interacting with the user device 170. In some implementations, one or more user devices 170 can be used by and/or included in the system 100.

While the control system 110 and the memory device 114 are described and shown in FIG. 1A as being a separate and distinct component of the system 100, in some implementations, the control system 110 and/or the memory device 114 are integrated in the user device 170 and/or the respiratory device 122. Alternatively, in some implementations, the control system 110 or a portion thereof (e.g., the processor 112) can be located in a cloud (e.g., integrated in a server, integrated in an Internet of Things (IoT) device, connected to the cloud, be subject to edge cloud processing, etc.), located in one or more servers (e.g., remote servers, local servers, etc., or any combination thereof.

While system 100 is shown as including all of the components described above, more or fewer components can be included in a system for generating physiological data and determining a recommended notification or action for the user according to implementations of the present disclosure. For example, a first alternative system includes the control system 110, the memory device 114, and at least one of the one or more sensors 130. As another example, a second alternative system includes the control system 110, the memory device 114, at least one of the one or more sensors 130, and the user device 170. As yet another example, a third alternative system includes the control system 110, the memory device 114, the respiratory system 120, at least one of the one or more sensors 130, and the user device 170. Thus, various systems can be formed using any portion or portions of the components shown and described herein and/or in combination with one or more other components.

Referring now to FIG. 1B, in some implementations the system 100 is communicatively connected to a computer network that is further communicatively connected to a remote server system 190. Through this implementation, the system 100 can transmit communications to and receive communications from the remote server system 190. For example, the system 100 may transmit instructions or commands (e.g., in the form of electronic or electromagnetic signals) over the computer network to provide certain modules desired by the system 100. Those commands are received by the remote server system 190. In response to the received commands, the remote server system 190 then transmits over the network the requested modules for receipt by the system 100.

The present disclosure is directed to systems and method for determining one or more health conditions from health data of a user of a respiratory system, such as a respiratory system 120 described for system 100. In some implementations, at least some of the health data can be generated and/or collected by the one or more sensors 130 during sleep sessions of a user of the respiratory system 120. The health data can be collected and stored in a memory device 114 of one or more processing devices local to the user, such as processor 112 or a processor that is part of a user device 170 (e.g., smartphone, tablet), respiratory system 120, or a sensor 130. In some implementations, health data can be received from a user or another entity (such as a physician or caregiver) via the control system 110, respiratory system 120, and/or a user device 170.

Figure 3:
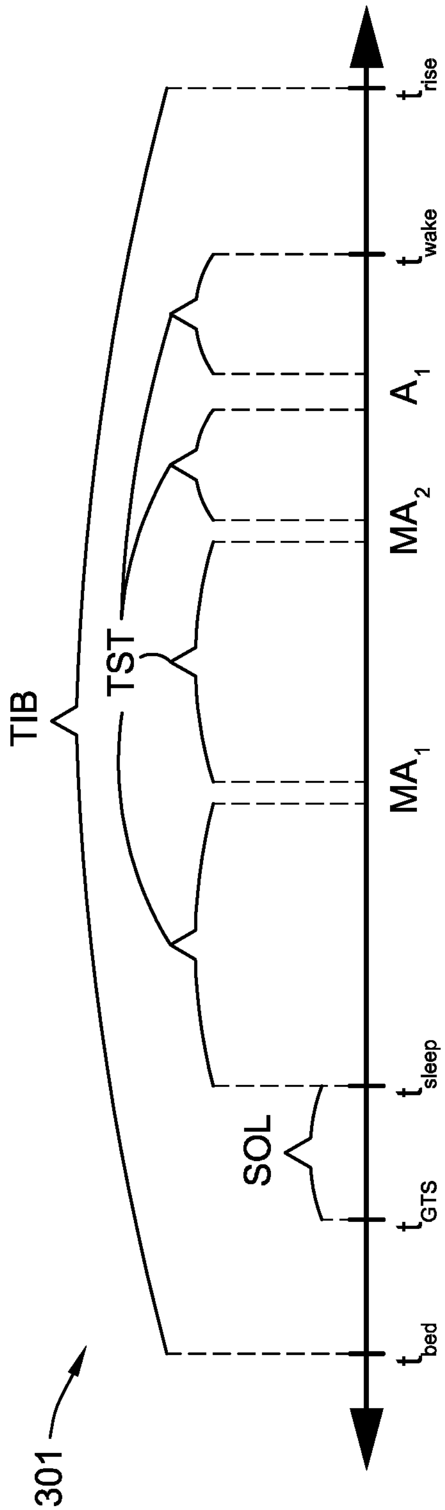
FIG. 3 illustrates an exemplary timeline for a sleep session during which health data is collected, according to some implementations of the present disclosure.
Figure 4:
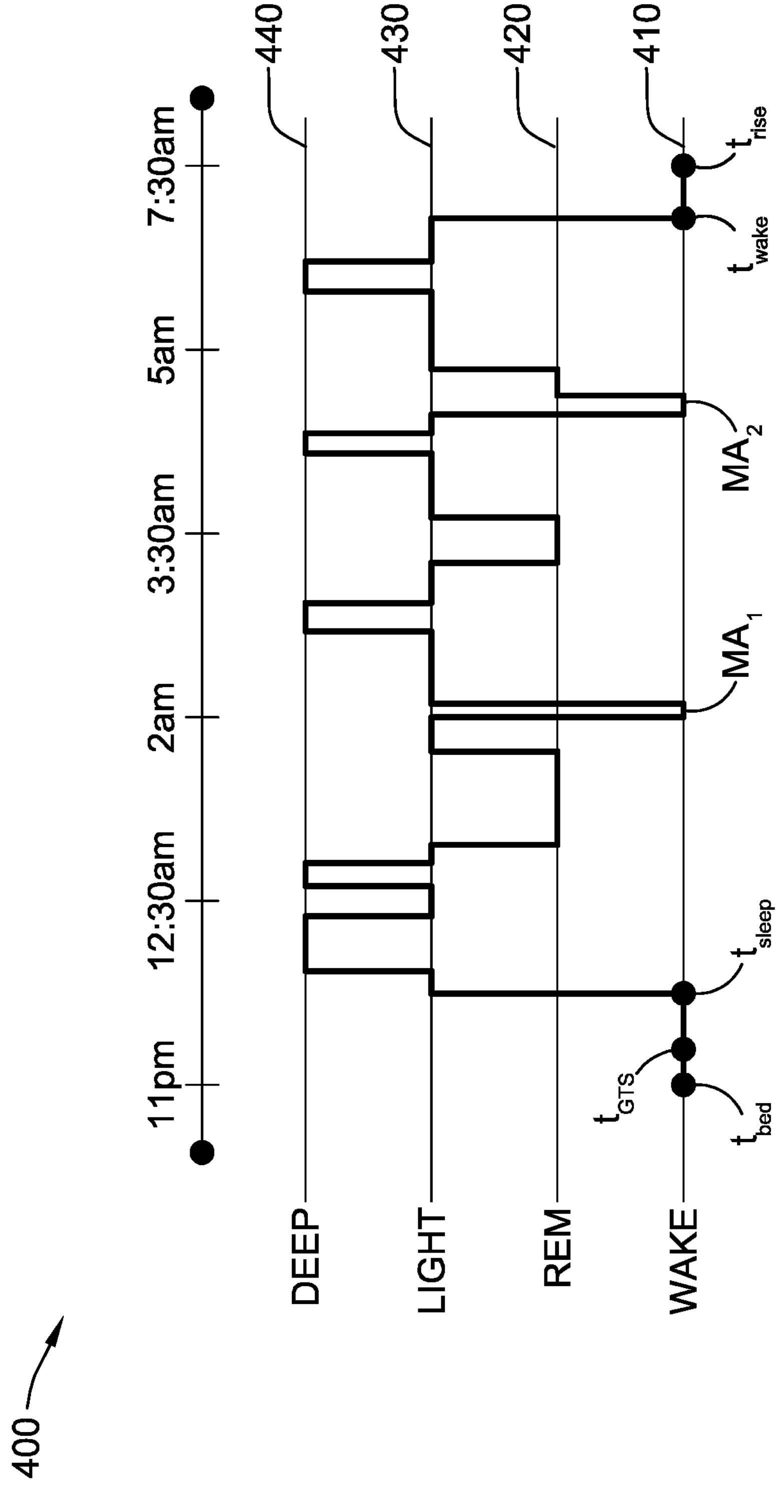
FIG. 4 illustrates an exemplary hypnogram associated with an analysis of health data collected during the sleep session of FIG. 3, according to some implementations of the present disclosure.

To illustrate the generation and collection of health data, an exemplary aspect for a sleep session during which select health data is collected is depicted in FIG. 3, along with an exemplary hypnogram in FIG. 4 that is associated with an analysis of the health data collected during the sleep session of FIG. 3. The data used to generate the exemplary depictions are generated from the sensor(s) 130.

As used herein, a sleep session can be defined in a number of ways based at least in part on, for example, an initial start time and an end time. In some implementations, a sleep session is a duration where the user is asleep, that is, the sleep session has a start time and an end time, and during the sleep session, the user does not wake until the end time. That is, any period of the user being awake is not included in a sleep session. From this first definition of sleep session, if the user wakes ups and falls asleep multiple times in the same night, each of the sleep intervals separated by an awake interval is a sleep session.

Alternatively, in some implementations, a sleep session has a start time and an end time, and during the sleep session, the user can wake up, without the sleep session ending, so long as a continuous duration that the user is awake is below an awake duration threshold. The awake duration threshold can be defined as a percentage of a sleep session. The awake duration threshold can be, for example, about twenty percent of the sleep session, about fifteen percent of the sleep session duration, about ten percent of the sleep session duration, about five percent of the sleep session duration, about two percent of the sleep session duration, etc., or any other threshold percentage. In some implementations, the awake duration threshold is defined as a fixed amount of time, such as, for example, about one hour, about thirty minutes, about fifteen minutes, about ten minutes, about five minutes, about two minutes, etc., or any other amount of time.

In some implementations, a sleep session is defined as the entire time between the time in the evening at which the user first entered the bed, and the time the next morning when user last left the bed. Put another way, a sleep session can be defined as a period of time that begins on a first date (e.g., Monday, Jan. 6, 2020) at a first time (e.g., 10:00 PM), that can be referred to as the current evening, when the user first enters a bed with the intention of going to sleep (e.g., not if the user intends to first watch television or play with a smart phone before going to sleep, etc.), and ends on a second date (e.g., Tuesday, Jan. 7, 2020) at a second time (e.g., 7:00 AM), that can be referred to as the next morning, when the user first exits the bed with the intention of not going back to sleep that next morning.

In some implementations, the user can manually define the beginning of a sleep session and/or manually terminate a sleep session. For example, the user can select (e.g., by clicking or tapping) one or more user-selectable element that is displayed on the display device 172 of the user device 170 (FIG. 1) to manually initiate or terminate the sleep session.

Referring to FIG. 3, an exemplary timeline 300 for a sleep session is illustrated. The timeline 300 includes an enter bed time ($t_{bed}$), a go-to-sleep time ($t_{GTS}$), an initial sleep time ($t_{sleep}$), a first micro-awakening MA1, a second micro-awakening MA2, an awakening A, a wake-up time ($t_{wake}$), and a rising time ($t_{rise}$).

The enter bed time bed is associated with the time that the user initially enters the bed (e.g., bed 230 in FIG. 2) prior to falling asleep (e.g., when the user lies down or sits in the bed). The enter bed time $t_{bed}$ can be identified based at least in part on a bed threshold duration to distinguish between times when the user enters the bed for sleep and when the user enters the bed for other reasons (e.g., to watch TV). For example, the bed threshold duration can be at least about 10 minutes, at least about 20 minutes, at least about 30 minutes, at least about 45 minutes, at least about 1 hour, at least about 2 hours, etc. While the enter bed time $t_{bed}$ is described herein in reference to a bed, more generally, the enter time $t_{bed}$ can refer to the time the user initially enters any location for sleeping (e.g., a couch, a chair, a sleeping bag, etc.).

The go-to-sleep time (GTS) is associated with the time that the user initially attempts to fall asleep after entering the bed ($t_{bed}$). For example, after entering the bed, the user may engage in one or more activities to wind down prior to trying to sleep (e.g., reading, watching TV, listening to music, using the user device 170, etc.). The initial sleep time ($t_{sleep}$) is the time that the user initially falls asleep. For example, the initial sleep time ($t_{sleep}$) can be the time that the user initially enters the first non-REM sleep stage.

The wake-up time $t_{wake}$ is the time associated with the time when the user wakes up without going back to sleep (e.g., as opposed to the user waking up in the middle of the night and going back to sleep). The user may experience one of more unconscious microawakenings (e.g., microawakenings MA1 and MA2) having a short duration (e.g., 5 seconds, 10 seconds, 30 seconds, 1 minute, etc.) after initially falling asleep. In contrast to the wake-up time $t_{wake}$, the user goes back to sleep after each of the microawakenings MA1 and MA2. Similarly, the user may have one or more conscious awakenings (e.g., awakening A) after initially falling asleep (e.g., getting up to go to the bathroom, attending to children or pets, sleep walking, etc.). However, the user goes back to sleep after the awakening A. Thus, the wake-up time $t_{wake}$ can be defined, for example, based at least in part on a wake threshold duration (e.g., the user is awake for at least 15 minutes, at least 20 minutes, at least 30 minutes, at least 1 hour, etc.).

Similarly, the rising time $t_{rise}$ is associated with the time when the user exits the bed and stays out of the bed with the intent to end the sleep session (e.g., as opposed to the user getting up during the night to go to the bathroom, to attend to children or pets, sleep walking, etc.). In other words, the rising time $t_{rise}$ is the time when the user last leaves the bed without returning to the bed until a next sleep session (e.g., the following evening). Thus, the rising time $t_{rise}$ can be defined, for example, based at least in part on a rise threshold duration (e.g., the user has left the bed for at least 15 minutes, at least 20 minutes, at least 30 minutes, at least 1 hour, etc.). The enter bed time $t_{bed}$ time for a second, subsequent sleep session can also be defined based at least in part on a rise threshold duration (e.g., the user has left the bed for at least 4 hours, at least 6 hours, at least 8 hours, at least 12 hours, etc.).

As described above, the user may wake up and get out of bed one more times during the night between the initial $t_{bed}$ and the final $t_{rise}$. In some implementations, the final wake-up time $t_{wake}$ and/or the final rising time $t_{rise}$ that are identified or determined based at least in part on a predetermined threshold duration of time subsequent to an event (e.g., falling asleep or leaving the bed). Such a threshold duration can be customized for the user. For a standard user which goes to bed in the evening, then wakes up and goes out of bed in the morning any period (between the user waking up ($t_{wake}$) or raising up ($t_{rise}$), and the user either going to bed ($t_{bed}$), going to sleep ($t_{GTS}$) or falling asleep ($t_{sleep}$) of between about 12 and about 18 hours can be used. For users that spend longer periods of time in bed, shorter threshold periods may be used (e.g., between about 8 hours and about 14 hours). The threshold period may be initially selected and/or later adjusted based at least in part on the system monitoring the user's sleep behavior.

The total time in bed (TIB) is the duration of time between the time enter bed time $t_{bed}$ and the rising time $t_{rise}$. The total sleep time (TST) is associated with the duration between the initial sleep time and the wake-up time, excluding any conscious or unconscious awakenings and/or micro-awakenings therebetween. Generally, the total sleep time (TST) will be shorter than the total time in bed (TIB) (e.g., one minute short, ten minutes shorter, one hour shorter, etc.). For example, referring to the timeline 300 of FIG. 3, the total sleep time (TST) spans between the initial sleep time $t_{sleep}$ and the wake-up time $t_{wake}$, but excludes the duration of the first micro-awakening $MA_1$, the second micro-awakening $MA_2$, and the awakening A. As shown, in this example, the total sleep time (TST) is shorter than the total time in bed (TIB).

In some implementations, the total sleep time (TST) can be defined as a persistent total sleep time (PTST). In such implementations, the persistent total sleep time excludes a predetermined initial portion or period of the first non-REM stage (e.g., light sleep stage). For example, the predetermined initial portion can be between about 30 seconds and about 20 minutes, between about 1 minute and about 10 minutes, between about 3 minutes and about 5 minutes, etc. The persistent total sleep time is a measure of sustained sleep, and smooths the sleep-wake hypnogram. For example, when the user is initially falling asleep, the user may be in the first non-REM stage for a very short time (e.g., about 30 seconds), then back into the wakefulness stage for a short period (e.g., one minute), and then goes back to the first non-REM stage. In this example, the persistent total sleep time excludes the first instance (e.g., about 30 seconds) of the first non-REM stage.

In some implementations, the sleep session is defined as starting at the enter bed time ($t_{bed}$) and ending at the rising time ($t_{rise}$), i.e., the sleep session is defined as the total time in bed (TIB). In some implementations, a sleep session is defined as starting at the initial sleep time ($t_{sleep}$) and ending at the wake-up time ($t_{wake}$). In some implementations, the sleep session is defined as the total sleep time (TST). In some implementations, a sleep session is defined as starting at the go-to-sleep time ($t_{GTS}$) and ending at the wake-up time ($t_{wake}$). In some implementations, a sleep session is defined as starting at the go-to-sleep time ($t_{GTS}$) and ending at the rising time ($t_{rise}$). In some implementations, a sleep session is defined as starting at the enter bed time ($t_{bed}$) and ending at the wake-up time ($t_{wake}$). In some implementations, a sleep session is defined as starting at the initial sleep time ($t_{sleep}$) and ending at the rising time ($t_{rise}$).

Referring to FIG. 4, an exemplary hypnogram 400 corresponding to the timeline 300 (FIG. 3), according to some implementations, is illustrated. As shown, the hypnogram 400 includes a sleep-wake signal 401, a wakefulness stage axis 410, a REM stage axis 420, a light sleep stage axis 430, and a deep sleep stage axis 440. The intersection between the sleep-wake signal 401 and one of the axes 410-440 is indicative of the sleep stage at any given time during the sleep session.

The sleep-wake signal 401 can be generated based at least in part on physiological data (e.g., one type of health data) associated with the user (e.g., generated by one or more of the sensors 130 described herein). The sleep-wake signal can be indicative of one or more sleep stages, including wakefulness, relaxed wakefulness, micro-awakenings, a REM stage, a first non-REM stage, a second non-REM stage, a third non-REM stage, or any combination thereof. In some implementations, one or more of the first non-REM stage, the second non-REM stage, and the third non-REM stage can be grouped together and categorized as a light sleep stage or a deep sleep stage. For example, the light sleep stage can include the first non-REM stage and the deep sleep stage can include the second non-REM stage and the third non-REM stage. While the hypnogram 400 is shown in FIG. 4 as including the light sleep stage axis 430 and the deep sleep stage axis 440, in some implementations, the hypnogram 400 can include an axis for each of the first non-REM stage, the second non-REM stage, and the third non-REM stage. In other implementations, the sleep-wake signal can also be indicative of a respiration signal, a respiration rate, an inspiration amplitude, an expiration amplitude, an inspiration-expiration amplitude ratio, an inspiration-expiration duration ratio, a number of events per hour, a pattern of events, or any combination thereof. Information describing the sleep-wake signal can be stored in the memory device 114.

The hypnogram 400 can be used to determine one or more sleep-related parameters, such as, for example, a sleep onset latency (SOL), wake-after-sleep onset (WASO), a sleep efficiency (SE), a sleep fragmentation index, sleep blocks, or any combination thereof.

The sleep onset latency (SOL) is defined as the time between the go-to-sleep time ($t_{GTS}$) and the initial sleep time ($t_{sleep}$). In other words, the sleep onset latency is indicative of the time that it took the user to actually fall asleep after initially attempting to fall asleep. In some implementations, the sleep onset latency is defined as a persistent sleep onset latency (PSOL). The persistent sleep onset latency differs from the sleep onset latency in that the persistent sleep onset latency is defined as the duration time between the go-to-sleep time and a predetermined amount of sustained sleep. In some implementations, the predetermined amount of sustained sleep can include, for example, at least 10 minutes of sleep within the second non-REM stage, the third non-REM stage, and/or the REM stage with no more than 2 minutes of wakefulness, the first non-REM stage, and/or movement therebetween. In other words, the persistent sleep onset latency requires up to, for example, 8 minutes of sustained sleep within the second non-REM stage, the third non-REM stage, and/or the REM stage. In other implementations, the predetermined amount of sustained sleep can include at least 10 minutes of sleep within the first non-REM stage, the second non-REM stage, the third non-REM stage, and/or the REM stage subsequent to the initial sleep time. In such implementations, the predetermined amount of sustained sleep can exclude any micro-awakenings (e.g., a ten second micro-awakening does not restart the 10-minute period).

The wake-after-sleep onset (WASO) is associated with the total duration of time that the user is awake between the initial sleep time and the wake-up time. Thus, the wake-after-sleep onset includes short and micro-awakenings during the sleep session (e.g., the micro-awakenings MA1 and MA2 shown in FIG. 4), whether conscious or unconscious. In some implementations, the wake-after-sleep onset (WASO) is defined as a persistent wake-after-sleep onset (PWASO) that only includes the total durations of awakenings having a predetermined length (e.g., greater than 10 seconds, greater than 30 seconds, greater than 60 seconds, greater than about 5 minutes, greater than about 10 minutes, etc.)

The sleep efficiency (SE) is determined as a ratio of the total time in bed (TIB) and the total sleep time (TST). For example, if the total time in bed is 8 hours and the total sleep time is 7.5 hours, the sleep efficiency for that sleep session is 93.75%. The sleep efficiency is indicative of the sleep hygiene of the user. For example, if the user enters the bed and spends time engaged in other activities (e.g., watching TV) before sleep, the sleep efficiency will be reduced (e.g., the user is penalized). In some implementations, the sleep efficiency (SE) can be calculated based at least in part on the total time in bed (TIB) and the total time that the user is attempting to sleep. In such implementations, the total time that the user is attempting to sleep is defined as the duration between the go-to-sleep (GTS) time and the rising time described herein. For example, if the total sleep time is 8 hours (e.g., between 11 PM and 7 AM), the go-to-sleep time is 10:45 PM, and the rising time is 7:15 AM, in such implementations, the sleep efficiency parameter is calculated as about 94%.

The fragmentation index is determined based at least in part on the number of awakenings during the sleep session. For example, if the user had two micro-awakenings (e.g., micro-awakening MA1 and micro-awakening MA2 shown in FIG. 4), the fragmentation index can be expressed as 2. In some implementations, the fragmentation index is scaled between a predetermined range of integers (e.g., between 0 and 10).

The sleep blocks are associated with a transition between any stage of sleep (e.g., the first non-REM stage, the second non-REM stage, the third non-REM stage, and/or the REM) and the wakefulness stage. The sleep blocks can be calculated at a resolution of, for example, 30 seconds.

In some implementations, the systems and methods described herein can include generating or analyzing a hypnogram including a sleep-wake signal to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof based at least in part on the sleep-wake signal of a hypnogram.

In other implementations, one or more of the sensors 130 can be used to determine or identify the enter bed time ($t_{bed}$), the go-to-sleep time ($t_{GTS}$), the initial sleep time ($t_{sleep}$), one or more first micro-awakenings (e.g., $MA_1$ and $MA_2$), the wake-up time ($t_{wake}$), the rising time ($t_{rise}$), or any combination thereof, which in turn define the sleep session. For example, the enter bed time $t_{bed}$ can be determined based at least in part on, for example, data generated by the motion sensor 138, the microphone 140, the camera 150, or any combination thereof. The go-to-sleep time can be determined at least in part based on, for example, data from the motion sensor 138 (e.g., data indicative of no movement by the user), data from the camera 150 (e.g., data indicative of no movement by the user and/or that the user has turned off the lights) data from the microphone 140 (e.g., data indicative of the using turning off a TV), data from the user device 170 (e.g., data indicative of the user no longer using the user device 170), data from the pressure sensor 132 and/or the flow rate sensor 134 (e.g., data indicative of the user turning on the respiratory device 122, data indicative of the user donning the user interface 124, etc.), or any combination thereof.

In the exemplary context of the health data collected and processed in FIGS. 3 and 4, it is contemplated that in addition to process the sleep stage of a user during a sleep session data could also be collected for heart rate. Trends from the collected health data can then be analyzed to determine if there is a correlation with a certain potential health condition and/or if the trends can be reconciled with other collected parameters such as user interface leakage, usage, residual AHI, etc.

It is contemplated that in addition to collecting and storing health data for a user of a respiratory system, the health data is processed on a device local to the user, such as on a respiratory device 122, user device 170, and/or related local control system 110 or processor 112. For example, an initial determination can be made of a potential health condition associated with the user based on the local analysis of the collected health data for the user.

If a potential health condition is identified, the disclosed methods and systems allow for receiving health assessment modules from a remote server to further assess the initially identified potential health condition. For example, the received health assessment modules may allow for the collection of additional health data and/or further analyses of already collected data to further refine or verify the initial determination of the potential health condition. With the health data and the analysis occurring on the local device, the present disclosure is particularly desirable as it aids with maintaining the privacy of a respiratory system user's personal health data. In some implementations, a received health assessment module, or another received module, includes instructions to alter the therapy settings of the respiratory device, and/or alter a component of the respiratory system such as the user interface (e.g. change from nasal to full facial mask), based on the verified determination of a health condition.

Individuals are often concerned about privacy including what happens to their personal data, such as how secure their health data is and who could gain access to it. The present disclosure solves a problem of how to handle privacy while also providing efficient, tailored services to a user of a respiratory system, such as the assessment of potential health conditions a user may have from the collected health data. The assessment can be completed entirely or nearly entirely on a device local to the user without health data needing to be shared, for example, with systems outside of the local systems controlled by the user. For example, a local device controlled by the user may receive very focused health assessment modules or a series of health assessment modules that may apply machine learning or artificial intelligence to analyze the localized health data and identify potential health condition(s) of the user based on the local analysis. The present disclosure minimizes, and in some instances may effectively eliminate, privacy concerns that develop when pushing sensitive health data for storage and/or analysis on a remote server system (e.g., the cloud). The benefit is that a user of a respiratory system can identify potential health conditions they may be unaware of and seek treatment without compromising their privacy. For example, a user may be notified by the system 100 of a verified determination of a potential health condition. This could be a visual, audio, or other human perceptible notification provided by, for example, a speaker, display, or haptic component of the respiratory device, an electronic device, etc. associated with the system 100. By providing the tailored service, the present disclosure increases the chances for positive healthcare outcomes for users of respiratory systems by identifying acute and chronic health conditions that the user may not be otherwise aware of.

In some implementations, health assessment modules are prepared and deployed to the respiratory system 120 or other devices local to the user, such as a user device 170, via over-the-air software updates. In some implementations, sensitive health data is stored locally for a set period after which it gets destroyed. In some implementations, only the last values determined from the collected health data are stored on the device local to the user. For example, if a health assessment module, or an initial assessment module (suitable for making the initial determination of the one or more potential health conditions), is searching for patterns in the health data, the full distribution of the health data may be stored without the specific values used to determine the distribution.

In some implementations, it is contemplated that certain health assessment applications or module-based systems may be stored continuously on a local device where the application or module is used more frequently for assessing a user's health data for a potential health condition. For health assessment applications or module-based systems that are used less frequently, the application or module may be received over a network from the remote server 190 and executed on the device local to the user. Once the processing step(s) involved in the assessment of a potential health condition are completed, the health assessment application or module can be deleted from the local device to conserve the local memory and processing resources. Monitoring and adjusting the bandwidth of local resources (e.g., memory utilization, processing utilization) provides a benefit when executing health assessment modules by allowing improved use of spare computing and/or memory resources to dynamically run application(s) and module(s) to generate features and insights from analyzed health data.

It is contemplated that the pooling of local processing and memory resources, such as the processing and memory components of the respiratory system (e.g., CPAP system, ventilator) and a user device (e.g., smartphone, tablet, smart-speaker, smart glasses, smart garments), can provide the needed computing power for applying machine-learning based health assessment modules to the collected health data. Furthermore, the user device in some aspects can also provide beneficial resources for tracking sensors and receiving sensor data.

In some implementations, the initial determination of a potential health condition, or the additional assessment by any received health assessment modules, may include artificial intelligence or machine learning algorithm(s) for analyzing select user health data collected by and stored on the device local to the user. For example, in some aspects, the different types of health data can be categorized into demographic, biometric, medical, self-reported, sleep parameter, and/or sensor data by running the health data through a decision tree. The data may include mechanical performance data, mask data, facial recognition data, time and/or duration of respiratory system use data, and system sensor data collected and/or stored on a device local to the user. After the data is parsed by the decision tree into certain categories, such as through an artificial intelligence algorithm, some data may get deleted and some data may remain stored locally. For example, once certain raw health data has been processed by the health assessment module, only the outcome of the assessment may remain relevant and is stored locally for further use and the raw data can then be deleted. In some implementations, at least some of the health data may be encrypted. In some implementations, select health data may be anonymized or de-identified and stored locally after processing when a health assessment module is completed.

In some implementations, a received health assessment module, that includes artificial intelligence or machine learning algorithm(s) for analyzing the collected health data, allows for the module to make inferences on the local device itself. The health assessment module may also access remote data sources in addition to local data sources, in order to make inferences on the local device. Such machine learning and artificial intelligence allows the module to train itself to look for specific types of health data or events that are personalized to the respiratory system user.

In some implementations, the collected and stored health data can be analyzed by artificial intelligence or machine learning that, for example, makes correlations for the data using a machine learning algorithm. The machine learning algorithm may implement machine learning structures such as a neural network, decision tree ensemble, support vector machine, Bayesian network, or gradient boosting machine. Such structures can be configured to implement either linear or non-linear predictive models for determining and assessing different health conditions. For example, data processing, such as determining the status of a respiratory system user's health condition, may be carried out by any one or more of supervised machine learning, deep learning, a convolutional neural network, and a recurrent neural network, whether such structures were configured before (e.g., based on a separate large pool of health data) or after (e.g., based on the user's personal health data) the health assessment module(s) were received on the processing device(s) local to the user. In some aspects, descriptive and predictive supervised machine learning with hand-crafted features are implemented by the machine learning algorithm. It is also contemplated that implemented machine learning algorithm(s) can use many more variables than hand-crafted features or simple decision trees.

Convolutional neural networks (CNNs) are used widely in audio and image processing for inferring information (such as for face recognition), and can also be applied to audio spectrograms, or even population scale genomic data sets created from the collected data represented as images. When carrying out image or spectrogram processing, the system cognitively "learns" temporal and frequency properties from intensity, spectral, and statistical estimates of the digitized image or spectrogram data.

In contrast to CNNs, not all problems can be represented with fixed-length inputs and outputs. For example, processing respiratory sounds or sounds of the heart has similarities with speech recognition and time series prediction. Thus, the sound analysis can benefit from a system to store and use context information such as recurrent neural networks (RNNs) that can take the previous output or hidden states as inputs. In other words, they may be multilayered neural networks that can store information in context nodes. RNNs allow for processing of variable length inputs and outputs by maintaining state information across time steps, and may include LSTMs (long short term memories, types of "neurons" to enable RNNs increased control over, which can be unidirectional or bidirectional) to manage the vanishing gradient problem and/or by using gradient clipping.

It is contemplated that the machine-learning algorithm may be trained for supervised learning of a known respiratory system user status from known data inputs to assist in analyzing input data. The machine-learning algorithm may also be trained for unsupervised learning to determine unknown correlations between input data and user status, to increase the range of analysis by a received health condition assessment module.

The collection of health data from a population beyond a single respiratory system user allows large population health data analyzed for the purpose of providing more accurate assessments of potential health conditions. The collected data may be used to refine artificial intelligence or machine learning algorithms that may be incorporated into a received health assessment module.

In some implementations, to allow the user of the respiratory system to maintain control over their collected and stored health data, the user of the respiratory system is prompted to provide permission for any of their health data to be transmitted from the storage and collection device(s) local to the user, or for request(s) to be sent to a remote server for health assessment module(s). In some aspects, the stored health data is encrypted.

Figure 5:
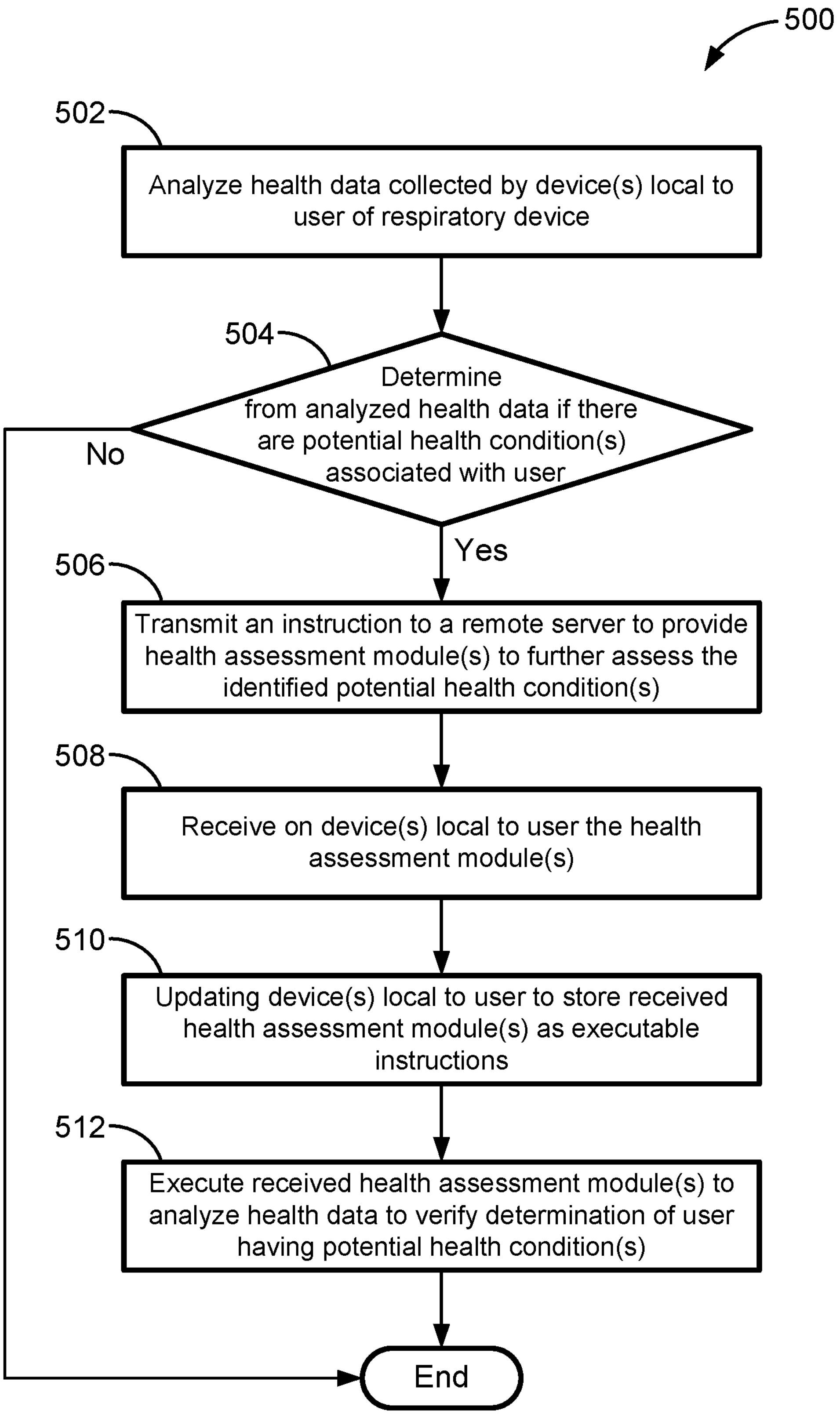
FIG. 5 is a process flow diagram for a method for determining health conditions of a user of a respiratory system from health data being collected, stored, and analyzed on a device local to the user, according to some implementations of the present disclosure.

Referring now to FIG. 5, a process flow diagram is depicted for a method 500 for determining a potential health condition of a user of a respiratory system based on health data collected, stored, and analyzed on a device local to the user. One or more steps of the method 500 can be implemented using any element or aspect of the system 100 (FIGS. 1A, 1B, and 2) described herein.

In addition to the many examples of health data described elsewhere herein, the health data of a user can include historical health data collected by the one or more processing devices from, for example, electronic medical/health record for the user and/or historical data received from one or more sensors 130. In some implementations, the health data of the user includes real-time data collected by the one or more processing devices based on, for example, data received from sensors 130. It is also contemplated that the health data of a user can include information received from the user, therapy data collected during respiratory system operation, user interface data, facial feature data, time and/or duration of respiratory system use data, speech data (including health data derived from speech processing and analysis), patient sensor data, sleep stage information, apnea hypopnea index, user demographic information, user physiological data, operational data of the respiratory system, or combinations thereof.

Step 502 of the method 500 includes analyzing health data of a user collected by a processing device local to the user of a respiratory system to make an initial determination of one or more potential health conditions associated with the user. In some implementations, the one or more processing devices local to the user can be a respiratory device of the respiratory system, an electronic device associated with the respiratory system, such as a user device, or both. In some implementations, the respiratory system can be a positive airway pressure therapy system or a ventilator. In some implementations, the electronic device is a mobile device (e.g., a smart phone) or a tablet controller connected to the respiratory system. In some implementations, the mobile device and the respiratory system may be wirelessly connected. In some implementations, the initial determination of the health condition can also include determining if the user is likely experiencing adverse effects the health condition.

In some implementations of the method 500, the electronic device associated with the respiratory system discussed above can provide additional services, via, for example, a rich user interface that can be highly interactive (e.g., a user interface, voice control, connection to and control of other smart home devices) and can also include a secure connection to the respiratory system and/or a cloud service, while keeping the sensitive data on device(s) local to the user. In some implementations, the electronic device can include a multitude of sensors, such as one of more of sensors 130 (e.g., acoustic sensors 141). In addition, it is contemplated that an electronic device such as a smart phone or tablet can aid the management of data privacy, including for the sharing of data between apps. For example, the collected health data could be shared with an online support program and app that automatically sends data from a respiratory system 120 to another computing device local to the user, such as a smart phone, in the form of a therapy score (e.g., myAir™) and/or a sleep score. The electronic device, such as the smart phone or tablet, can be connected to the respiratory system by a wireless technology, such as Bluetooth™ for sensitive data that is not transmitted by the respiratory system to the cloud (e.g., the Airview™ secure, cloud-based patient management system for online patient monitoring) via a cellular or other wireless connection. For example, the myAir™ app by ResMed can obtain a health assessment module (and, optionally, a treatment module) from the cloud, and determine what should be uploaded to the respiratory system to run locally or in an app sandbox on the smartphone, and thus preserves the privacy of the user. As another example, flow data or data from user interface sensor(s) might be downloaded in order to process for cardiac-related health issues. In some implementations, the data sent to the cloud server can be limited and include, for example, that a service was activated. The outcome of the health assessment module analysis can then be shared with a third-party, such as an integrated care provider, a private cardiologist, a web-based medical service provider, etc., that could provide a screening service by, for example, supplying a cardiac ECG monitor, a glucose monitor, a blood pressure monitor, or an analyte monitor to the user.

In some implementations, a health condition for which an initial determination is made from the collected health data can include one or more of a heart condition, edema, hypertension, or chronic obstructive pulmonary disease. Other health conditions can include atrial fibrillation, drug-resistant hypertension, diabetes, overlap of obstructive sleep apnea and chronic obstructive pulmonary disease, obstructive sleep apnea, apneas, a central apnea, a mixed apnea, hypopnea, chronic heart failure, stroke, obesity, metabolic syndrome, depression, coronary artery disease, asthma, periodic limb movement (PLM), Restless Leg Syndrome (RLS), Sleep-Disordered Breathing (SDB), Cheyne-Stokes Respiration (CSR), respiratory insufficiency, Obesity Hyperventilation Syndrome (OHS), Neuromuscular Disease (NMD), and chest wall disorders. In some implementations, the initial determination of the health condition can also include determining if the user is likely experiencing adverse effects the health condition.

In some implementations, a heart condition can be determined from the respiratory system (e.g. PAP system), based on detection of cardiac output from estimations of carbon dioxide, using processing of a microphone signal. In some implementations, a heart condition could also, or alternatively, be based on the processing of one or more of cardiogenic oscillations in a flow signal, heart rate, oxygen saturation, pulse transit time, or blood pressure from a pulse oximeter which may be coupled to the respiratory system. In some implementations, a heart condition could also, or alternatively, be based on the processing of one or more of signals from a separate mattress sensor or a wearable device. In some implementations, a heart condition can be determined by accessing an electronic health record.

In some implementations, edema can be detected by assessing weight gain from, for example, a weighing scale, or via processing of an image or video from a smartphone camera, such as from a photo taken of the legs to determine swelling.

In some implementations, hypertension can be detected or determined via blood pressure sensing from a blood pressure cuff monitor, a finger-worn device, a watch, or other sensing apparatus. In some implementations, hypertension can be detected or determined from an electronic health record, or other blood pressure sensing modalities, such as derivation from video based PPG.

In some implementations, chronic obstructive pulmonary disease can be detected or determined via respiration rate and inspiration/expiration ratio from a respiratory system flow sensor, from a wearable device such as a watch or patch or earring, or a cough monitor based on sound processing etc.

In some implementations, other health conditions that can be detected or determined include atrial fibrillation, that can be detected via an irregular heart beat sensed by a respiratory system flow sensor (cardiogenic oscillation), from an optical PPG sensor, from an ECG sensor (e.g., in a watch or patch or chest electrodes), from a sensor in a user interface and so forth. Drug-resistant hypertension can be detected or determined based on input from an electronic health record, along with related blood pressure measurements from the electronic health record or as measured by a sensor. Diabetes can be detected or determined based on a blood or optical based measure of blood glucose, or based on gas analysis of exhaled air into a user interface. Overlap of obstructive sleep apnea and chronic obstructive pulmonary disease can be detected or determined by relating respiratory system data to COPD detection data. Central apnea can be detected or determined by the respiratory system, such as by using forced oscillation to determine if airway is collapsed or not, or by a separate sensor looking for a cessation of breathing without paradoxical breathing. Mixed apnea can be detected or determined as a mix of central and obstructive events in a similar manner.

In some implementations, additional other health conditions that can be detected or determined include chronic heart failure that can be detected based on changes in heart rate, cardiac output, edema and so forth, and a detected worsening in one of these parameters. Stroke can be detected or determined based on an increase in atrial fibrillation or detected flutter, or other cardiac arrhythmias. Depression can be detected or determined based on changes in heart rate trends derived from a heart rate sensor that are compared to those in people without depression. Coronary artery disease can be detected or determined based on cardiac output data. Asthma can be detected or determined based on changes in breathing rate (e.g., increases in breathing rate). Periodic limb movement (PLM) and Restless Leg Syndrome (RLS) can be detected or determined based on different movement signatures in the respiratory system flow or microphone signal, or by a separate movement sensor. Cheyne-Stokes Respiration (CSR) is a form of periodic breathing, typical of central apnea, and can be detected or determined from a characteristic waxing and waning amplitude modulated shape that can be determined from a respiratory system flow signal or a standalone contact or non-contact breathing sensor.

The health data relating to the health conditions disclosed herein may be communicated directly to, via wired or wireless communication, and collected by the memory of one or more processing devices local to the user. Additionally, or alternatively, the health data may be inputted to the one or more processing devices by the user, a physician or caregiver, obtained from an electronic medical/health record, or any combination thereof.

At step 504 of the method 500, if it is determined that there are no potential health condition(s) associated with the user of the respiratory system, the method ends. However, if it is initially determined that the user of the respiratory system has one or more potential health conditions, the method proceeds to step 506. In some implementations, if the initial determination for assessing whether a user has a potential health condition is inconclusive, the method will proceed to step 506. In some implementations, an initial determination of a potential health condition may have a confidence level assigned to determine if there is a potential health condition. For example, in some aspects, if the initial determination assigns a 50 percent or greater confidence level (e.g., zero percent means there is no health condition and 100 percent mean there is a health condition) to there being a potential health condition, the method proceeds to step 506. But, if the confidence level falls below 50 percent, the method ends. It is contemplated that in some implementations the confidence level threshold for deciding whether there is a potential health condition will vary (e.g., 20 percent, 25 percent, 30 percent, 40 percent, 55 percent, 60 percent, 70 percent, 75 percent, and so forth). In some implementations, the confidence level threshold for initially determining if there is a potential health condition can also vary depending on the immediacy of adverse health effects of the potential health condition (e.g., an acute versus a chronic health condition)

Step 506 of the method 500 is implemented in response to making an initial determination that one or more potential health conditions are associated with a user based an analysis of health data collected by and stored in the memory of the processing device(s) local to the user. Step 506 includes transmitting a command to a remote server to provide one or more health assessment modules that includes instructions for analyzing the health data to further assess the initially determined one or more potential health conditions. The instruction is transmitted over a computer network to which the system 100 and the remote server are both connected, as depicted, for example, in FIG. 1B. In some implementations, the transmitted command to provide one or more health assessment modules includes an instruction to provide at least one additional module to obscure a specific health assessment module associated with a determined potential health condition of the user. For example, if a module is directed to assessing the health data further to determine if the user has a heart condition, the transmitted command(s) can include a request for modules for assessing a heart condition and asthma. The asthma module is used to obscure or mask the flagged health condition that the user may have where it would be difficult to correctly assign a certain health condition to a particular user, thus further aiding in maintaining the privacy of the user's health data and/or health condition. In some implementations, the transmitting of the command to provide one or more health assessment modules is executed by the respiratory device 122, the electronic device (e.g., an electronic user device 170), or both.

In some exemplary implementations, a health assessment module can include instructions for detecting the worsening of a pre-existing health condition, or detecting the emergence of a new health issue or health condition. For example, in some cases, one or more pre-existing or new conditions may be present, such as a person having known OSA and drug managed hypertension, where atrial fibrillation or drug resistant hypertension might be detected by the health assessment module. In some exemplary implementations, a health assessment module can include instructions for detecting a decompensation in heart failure or exacerbation in COPD, such as due to a viral or bacterial illness (e.g., influenza, Covid-19) such that a determination is made that the patient should receive further treatment or be hospitalized.

Step 508 of method 500 includes receiving the one or more health assessment modules on the one or more processing devices local to the user, such as the respiratory device 122, the user device 170, the memory device 114, the control system 110, or combinations thereof. The modules are received in response to the health assessment module(s) being provided by the remote server system 190 (see FIG. 1B). In some implementations, the received health assessment module(s) include a machine learning algorithm for analyzing select health data, such as all or a portion of the health data, of the respiratory system user. In some implementations, the received health assessment module(s) include at least one additional module to obscure a specific health assessment module associated with the initially determined potential health condition of the user. For example, if requested module is directed to further assessing the health data to determine if the user has an overlap of obstructive sleep apnea and chronic obstructive pulmonary disease heart condition, the received modules can include first module for assessing the overlap of obstructive sleep apnea and chronic obstructive pulmonary disease and a second module for assessing hypertension. The hypertension module is used to obscure or mask the flagged potential health condition.

In some implementations, the health assessment module is a mobile device app. In some implementations, the health assessment module is a component of an existing app, integrated into an existing app, or a standalone app. The health assessment module or existing app may be stored on a smartphone or other mobile device, or stored on a respiratory device.

Step 510 of the method 500 includes updating the one or more processing devices local to the user to store the one or more health assessment modules as executable instructions. For example, the updating of the processing devices to store the health assessment module can occur on one or more of the respiratory device 122, the user device 170, or the memory device 114 in combination with the control system 110.

Step 512 of the method 500 includes executing one or more of the received health assessment modules to analyze the health data to verify the initial determination of the user having one or more potential health conditions. The executing of the health assessment modules can occur on one or more of the devices that were updated in step 510. In some implementations, analysis of the health data by the one or more received health assessment modules includes assessing if the one or more health conditions are present. In some implementations, the analysis of the health data by the one or more received health assessment modules includes assessing if the user is likely experiencing adverse effects from a health condition determined to be present. In some aspects, the received health assessment module(s) includes instructions to collect additional health data of the user.

In some implementations of method 500, a de-identified summary report is prepared based on the assessed health data of the user. In some aspects, the de-identified summary report may be transmitted from the one or more processing devices local to the user for receipt by the remote server or a different server. In some aspects, an input may be received from the user indicating an authorization or permission to transmit the de-identified summary report or a portion thereof to the remote server or the different server. In some aspects, the de-identified summary report, or a portion thereof, may be encrypted prior to being transmitted. It is contemplated that the remote server or the different server may be associated in some aspects with a data escrow, a respiratory system manufacturer, or a healthcare provider.

In some implementations of method 500, a notification associated with a transmitted de-identified summary report is received on one or more processing devices local to a respiratory system user. In some aspects, the notification is for a de-identified health assessment module update.

In some implementations of method 500, a health assessment module can include a treatment module that is executed on a respiratory system (e.g., respiratory system 120). In other implementations, a treatment module can be received on a device local to a user (e.g., respiratory system 120) as separate step(s) in response to the treatment module being provided by a remote server. The treatment module can include one or more instructions for implementation on the respiratory system to provide respiratory therapy for a particular health condition associated with the use that was determined from the analysis of collected health data. The respiratory system is updated to store the received treatment module and executed to provide a modification to an existing respiratory therapy being delivered to the user by the respiratory system. In some implementations, the treatment module is contemplated to include a cognitive behavior therapy for insomnia (CBTi) module as one non-limiting example. In some implementations, the user via a device local to the user (e.g., respiratory system, smart phone) may connect to and communicate with a remote de-identified CBTi software-as-a-service (SaaS) provider associated with the treatment module.

In some aspects, a system includes a control system with one or more processors, and a memory having stored thereon machine readable instructions. The control system is coupled to the memory where the method 500 is implemented when the machine executable instructions in the memory are executed by at least one of the one or more processors of the control system.

In some aspects, a system for determining health conditions from health data of a user of a respiratory system includes a control system having one or more processors configured to implement the method 500.

In some aspects, a computer program product includes instructions which, when executed by a computer, cause the computer to carry out the method 500. The computer program product may be a non-transitory computer readable medium.

In some implementations, steps 502 to 512, including one or more of the additional implementations or aspects, can be repeated. For example, it is contemplated that the health condition of a respiratory user changes over time where different or more focused health assessment modules may be received and executed on the device local to the user.

Figure 6:
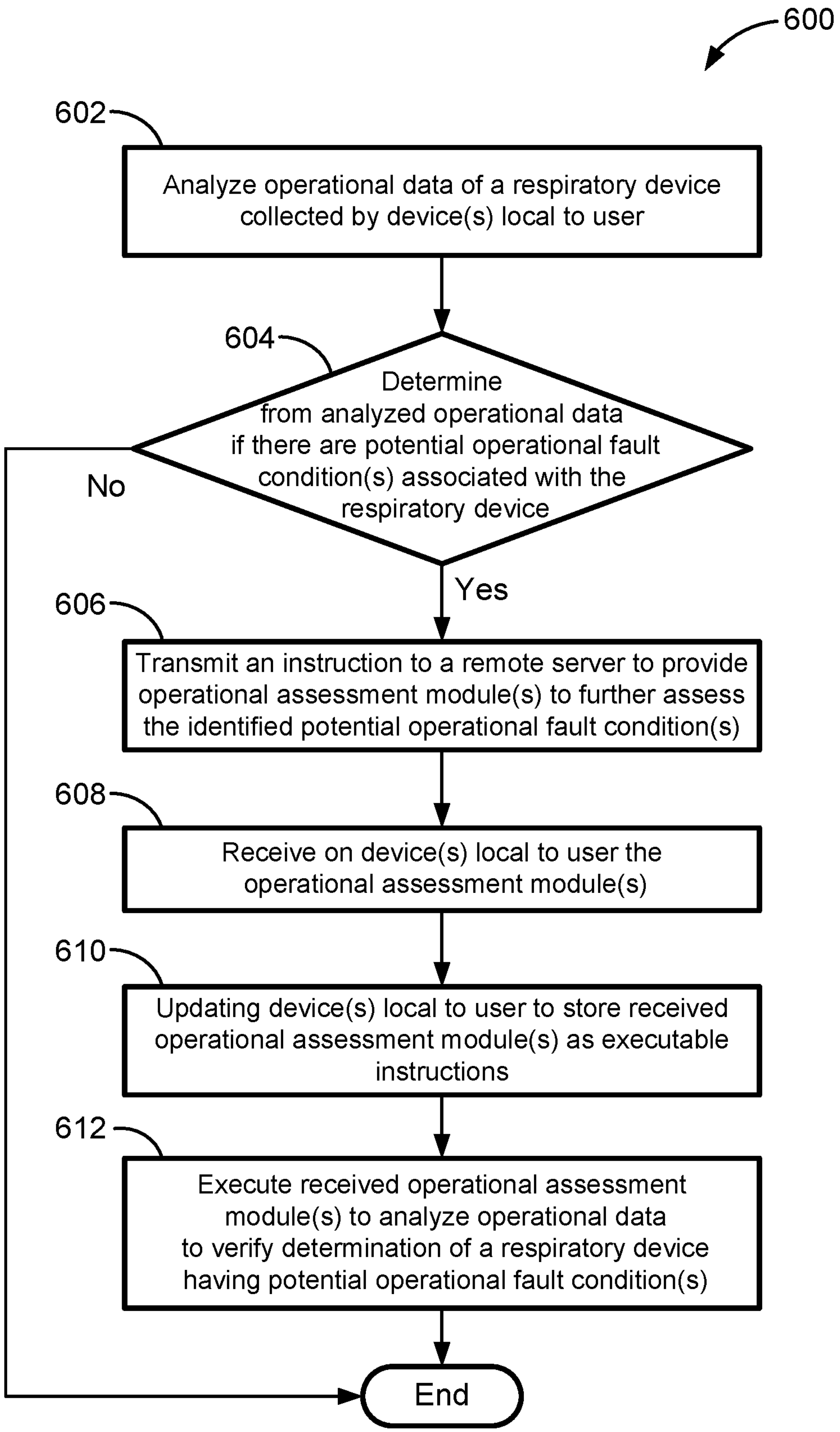
FIG. 6 is a process flow diagram for a method for determining operational fault conditions of a user of a respiratory system from operational data being collected, stored, and analyzed on a device local to the user, according to some implementations of the present disclosure.

Referring now to FIG. 6, a process flow diagram is depicted for a method 600 for determining a potential operational fault condition of a respiratory system from operational data being collected, stored, and analyzed on a device local to the user. One or more steps of method 600 can be implemented using any element or aspect of the system 100 (FIGS. 1A, 1B, and 2) described herein.

Examples of operational data can include historical operational data collected for the respiratory system, or a component of the respiratory system such as the respiratory device, conduit or user interface. In some implementations, the operational data of the respiratory system includes real-time data collected by the one or more processing devices based on, for example, data received from sensors 130. It is also contemplated that the operational data of a respiratory system includes information about the health of the motor, pressures, user data, humidifier data, conduit data, user interface data, environmental data, power supply data, display data, flow sensor data, and general information about the respiratory system to monitor how various system parameters change over time.

Step 602 of the method 600 includes analyzing operational data for a respiratory system where the data is collected on a device local to the user. The operational data is used to make an initial determination of one or more potential operational fault conditions associated with the respiratory system. In some implementations, the one or more processing devices local to the user can be a respiratory system, an electronic device associated with the respiratory system, such as a user device, or both. In some implementations, the respiratory system can be a positive airway pressure therapy system or a ventilator. In some implementations, the electronic device is a mobile device (e.g., a smart phone) or a tablet controller connected to the respiratory system. In some implementations, the mobile device and the respiratory system may be wirelessly connected. In some implementations, the initial determination of the operational fault condition can also include determining if the respiratory system is likely experiencing adverse effects due to the operational fault condition.

In some implementations of the method 600, the electronic device associated with the respiratory system discussed above can provide additional services, via, for example, a rich user interface that can be highly interactive (e.g., a user interface, voice control, connection to and control of other smart home devices) and can also include a secure connection to the respiratory system and/or a cloud service, while keeping the sensitive data on device(s) local to the user. In some implementations, the electronic device can include a multitude of sensors, such as one of more of sensors 130 (e.g., acoustic sensors 141). In addition, it is contemplated that an electronic device such as a smart phone or tablet can aid the management of data privacy, including for the sharing of data between apps. For example, the collected operational data could be shared with an online support program and app that automatically sends data from a respiratory system 120 to another computing device local to the user, such as a smart phone. The electronic device, such as the smart phone or tablet, can be connected to the respiratory system by Bluetooth™ for some sensitive data that is not transmitted by the respiratory system to the cloud (e.g., the Airview™ secure, cloud-based patient management system for online patient monitoring) via a cellular or other wireless connection. For example, an app can obtain an operational assessment module from the cloud, and determine what should be uploaded to the respiratory system to run locally or in an app sandbox on the smartphone, and thus preserves the privacy of the user. For example, flow data, pressure data, acoustic data or other operational data from the respiratory system might be downloaded in order to process for various operational issues. In some implementations, the data sent to the cloud server can be limited and include that a service was activated. The outcome of the operational assessment module analysis can then be shared with a third-party, such as an integrated care provider, respiratory system manufacturer, etc., optionally followed by a transmission of a patch, software update, etc. back to the respiratory system or associated electronic device.

In some implementations, an operational fault condition for which an initial determination is made from the collected operational data can include one or more of a motor defect, a pressure issue, a user annoyance issue, a humidifier issue, a conduit issue, a user interface issue, a power supply defect, an electrical connection issue, a display issue, or a flow sensor issue.

In some implementations, a motor defect can be determined or detected by collecting operational data about the health of a motor within the respiratory device. For example, the health of a respiratory device motor can be determined by comparing acoustic signature data using comparison tools, such as direct spectral estimation or echo cepstrum processing. These tools can be used, along with the lifetime use hours for the respiratory device, by comparing the signature of the actual blower motor performance after a certain lifetime use with known signatures at that same lifetime use for a normally operating blower motor. A determined acoustic signature can then be analyzed based on where on a distribution the actual blower motor lies compared to the known performance of a normally operating blower motor. A determination of potential early failure of the blower motor of the respiratory device can then be made based on the comparisons. It is also contemplated that potential acute failures of a blower motor can be determined or detected by assessing any sudden changes in signatures from a baseline or expected behavior of the blower motor. Such sudden changes may be indicative of motor failure due to a defect or damage to the respiratory device, such as through mishandling or water damage. A received operational fault assessment module can then be executed to diagnose a newly identified issue type or implement a cluster analysis of a fleet, or production batch, of respiratory devices.

In some implementations, a pressure issue can be determined or detected by collecting operational data related to pressures within a respiratory device. For example, a respiratory device may be producing insufficient pressures as a result of a blower motor or filter issues. A received operational fault assessment module can be executed to diagnose for motor issues or to diagnose for a blocked filter based on abnormal motor and noise behaviors of the respiratory device that could relate to pressure or air flow issues.

In some implementations, a user annoyance issue can be determined or detected by collecting operational data related to changes in motor acoustic signatures. For example, some acoustic changes may be potentially annoying to a user causing a decrease in usage of the respiratory system. While the acoustic change in the operation of the motor may not affect the actual therapy of the user of the respiratory system, the annoyance factor can lead to decreased adherence to therapy where identification of the issue is desirable.

In some implementations, a humidifier issue can be determined or detected by collecting operational data from the humidifier. For example, collecting data on noises based on the amount of water, or a lack of water, can be compared with known acoustic signatures to possibly trigger an operational fault. In another example, a determination can be made if a heater or sensor associated with the humidifier has failed. In yet another example, a determination can be made if expected acoustic signatures associated with a humidifier are not present despite the respiratory device having requested humidification. In some aspects, such acoustic signatures may be different because of the deterioration of a seal for the humidifier.

In some implementations, a conduit issue can be determined or detected by collecting operational data such as sensor or acoustic signatures related to the conduit. For example, a conduit may have a poor connection to the respiratory device that may cause a leak. Such a leak may be detected where acoustic signatures do not match those of a properly connected conduit, or where pressure sensors determine there is a lower than expected pressure in or near the conduit.

In some implementations, a power supply defect can be determined or detected by collecting operational data directed to, for example, noise or abnormal acoustic signatures. Such abnormal acoustic signatures may, for example, be suggestive of unexpected coil whine or changes in coil whine. The changes in acoustic signatures can indicate an early onset of power supply failure or possible safety risks. The changes in acoustic signature could also be due to power supply circuitry issues on the printed circuit board of the respiratory device or due to observed changes in supply voltages.

In some implementations, an electrical connection issue can be determined or detected by collecting operational data directed to, for example, noises or abnormal acoustic signature indicative of an electrical connection issue. For example, the operational data may relate to unexpected stop/start indications on the respiratory device.

In some implementations, a display issue can be determined or detected by collecting operational data direct to, for example, noise or abnormal acoustic signatures from, for example, a noisy backlight in a display. Display diagnostics may be received and implemented to determine such an operational fault.

In some implementations, a flow sensor issue can be determined or detected by collecting operational data such as flow sensor data and acoustic signatures for the sounds of the respiratory device. For example, an operational fault may be determined where the sound of the respiratory device does not match flow or pressure sensor readings or blower motor speed (e.g., rpm) readings. Additional assessment after determining the presence of such mismatches would be desirable to further determine if there is a component failure, reading error, or a sensor error in the respiratory device.

The operational data relating to the operational fault conditions disclosed herein may be communicated directly to, via wired or wireless communication, and collected by the memory of one or more processing devices local to the user. Additionally, or alternatively, the operational data may be inputted to the one or more processing devices by the user, a physician or caregiver, or any combination thereof.

In some aspects, building a machine learning model of blower motor and humidifier noise or acoustic signatures over time can be implemented. For example, such a machine learning model could then be applied as part of an initial determination of an operational fault or as part of an operational fault assessment module. The machine learning model can be developed over an expected life expectancy of a respiratory system and can include monitoring of how operational parameters vary over time.

At step 604 of the method 600, if it is determined that there are no potential operational fault condition(s) associated with the respiratory system, the method ends. However, if it is initially determined that the respiratory system has one or more potential operational fault conditions, the method proceeds to step 606. In some implementations, if the initial determination for assessing whether a respiratory system has a potential operational fault condition is inconclusive, the method will proceed to step 606. In some implementations, an initial determination of a potential operational fault condition may have a confidence level assigned to determine if there is a potential operational fault condition. For example, in some aspects, if the initial determination assigns a 50 percent or greater confidence level (e.g., zero percent means there is no operational fault condition and 100 percent mean there is an operational fault condition) to there being a potential operational fault condition, the method proceeds to step 606. But, if the confidence level falls below 50 percent, the method ends. It is contemplated that in some implementations the confidence level threshold for deciding whether there is a potential operational fault condition will vary (e.g., 20 percent, 25 percent, 30 percent, 40 percent, 55 percent, 60 percent, 70 percent, 75 percent, and so forth). In some implementations, the confidence level threshold for initially determining if there is a potential operational fault condition can also vary depending on the immediacy of adverse effects of the potential operational fault condition (e.g., the respiratory system will cease normal operations in the short-term versus a longer-term operational condition).

Step 606 of the method 600 is implemented in response to making an initial determination that one or more potential operational fault conditions are associated with a respiratory system based an analysis of operational data collected by and stored in the memory of the processing device(s) local to the user. Step 606 includes transmitting a command to a remote server to provide one or more operational fault assessment modules that include instructions for analyzing the operational data to further assess the initially determined one or more potential operational fault conditions. The command is transmitted over a computer network to which the system 100 and the remote server are both connected, as depicted, for example, in FIG. 1B. In some implementations, the transmitted command to provide one or more operational fault assessment modules includes an instruction to provide at least one additional module to obscure a specific operational fault assessment module associated with a determined potential operational fault condition of the respiratory system. For example, if a module is directed to assessing the operational data further to determine if the respiratory system has a pressure issue, the transmitted command(s) can include a request for modules for assessing a pressure issue and humidifier issue. The humidifier issue module is used to obscure or mask the flagged operational fault condition where it would be difficult to correctly assign a certain operational fault condition, thus further aiding in maintaining the privacy of the operational data associated with a user's respiratory system. In some implementations, the transmitting of the command(s) to provide one or more operational fault assessment modules is executed by the respiratory device 122, the electronic device (e.g., an electronic user device 170), or both.

Step 608 of method 600 includes receiving the one or more operational fault assessment modules on the one or more processing devices local to the user, such as the respiratory device 122, the user device 170, the memory device 114, the control system 110, or combinations thereof. The modules are received in response to the operational fault assessment module(s) being provided by the remote server system 190 (see FIG. 1B). In some implementations, the received operational fault assessment module(s) include a machine learning algorithm for analyzing select operational data, such as all or a portion of the operational data, of the respiratory system. In some implementations, the received operational fault assessment module(s) include at least one additional module to obscure a specific operational fault assessment module associated with the initially determined potential operational fault condition of the respiratory system. For example, if a requested module is directed to further assessing the operational data to determine if the respiratory system has a user annoyance issue, the received modules can include a first module for assessing the user annoyance issue and a second module for assessing a motor defect. The motor defect module is used to obscure or mask the flagged potential operational fault condition.

In some implementations, the operational fault assessment module is a mobile device app. In some implementations, the operational fault assessment module is a component of an existing app, integrated into an existing app, or a standalone app. The operational fault assessment module or existing app may be stored on a smartphone or other mobile device, or stored on a respiratory device.

Step 610 of the method 600 includes updating the one or more processing devices local to the user to store the one or more operational fault assessment modules as executable instructions. For example, the updating of the processing devices to store the operational fault assessment module can occur on one or more of the respiratory device 122, the user device 170, or the memory device 114 in combination with the control system 110.

Step 612 of the method 600 includes executing one or more of the received operational fault assessment modules to analyze the operational data to verify the initial determination of the respiratory system having one or more potential operational fault conditions. The executing of the operational fault assessment modules can occur on one or more of the devices that were updated in step 510. In some implementations, analysis of the operational data by the one or more received operational fault assessment modules includes assessing if the one or more operational fault conditions are present. In some implementations, the analysis of the operational data by the one or more received operational fault assessment modules includes assessing if the respiratory system is likely experiencing adverse effects from an operational fault condition determined to be present. In some aspects, the received operational fault assessment module(s) include instructions to collect additional operational data of the respiratory system. In some implementations, a received operational fault assessment module, or another received module, includes instructions to alter the operational settings of the respiratory device, and/or alter a component of the respiratory system such as the user interface (e.g. replace or repair the user interface), based on the verified determination of an operational fault condition.

In some implementations of method 600, a de-identified summary report is prepared based on the assessed operational data of the respiratory system. In some aspects, the de-identified summary report may be transmitted from the one or more processing devices local to the user for receipt by the remote server or a different server. In some aspects, an input may be received from the user indicating an authorization or permission to transmit the de-identified summary report or a portion thereof to the remote server or the different server. In some aspects, the de-identified summary report may be encrypted prior to being transmitted. It is contemplated that the remote server or the different server may be associated in some aspects with a data escrow, a respiratory system manufacturer, or a healthcare provider.

In some implementations of method 600, a notification associated with a transmitted de-identified summary report is received on one or more processing devices local to a respiratory system user. In some aspects, the notification is for a de-identified operational fault assessment module update.

In some aspects, a system includes a control system with one or more processors, and a memory having stored thereon machine readable instructions. The control system is coupled to the memory where the method 600 is implemented when the machine executable instructions in the memory are executed by at least one of the one or more processors of the control system.

In some aspects, a system for determining operational fault conditions from operational data of a respiratory system includes a control system having one or more processors configured to implement the method 600.

In some aspects, a computer program product includes instructions which, when executed by a computer, cause the computer to carry out the method 600. The computer program product may be a non-transitory computer readable medium.

In some implementations, steps 602 to 612, including one or more of the additional implementations or aspects, can be repeated. For example, it is contemplated that potential operational fault conditions of a respiratory system change over time where different or more focused operational fault assessment module may be received and executed on the device local to the user.

One or more elements or aspects or steps, or any portion(s) thereof, from one or more of any of the claims below can be combined with one or more elements or aspects or steps, or any portion(s) thereof, from one or more of any of the other claims below or combinations thereof, to form one or more additional implementations and/or claims of the present disclosure.

While the present disclosure has been described with reference to one or more particular embodiments or implementations, those skilled in the art will recognize that many changes may be made thereto without departing from the spirit and scope of the present disclosure. Each of these implementations and obvious variations thereof is contemplated as falling within the spirit and scope of the present disclosure. It is also contemplated that additional implementations according to aspects of the present disclosure may combine any number of features from any of the implementations described herein.

What is claimed is:

1. A method for determining a health condition from data generated by one or more sensors of a respiratory system, the data being collected by and stored in a memory of one or more processing devices local to a user, the method comprising:

analyzing the data collected by the one or more processing devices local to the user to make an initial determination of the health condition associated with the user of the respiratory system, the initial determination including assigning a confidence level to the health condition;

in response to the confidence level meeting a confidence level threshold, transmitting a command for receipt by a remote server to provide one or more assessment modules including instructions for analyzing the data to further assess the initially determined health condition;

in response to the one or more assessment modules being provided by the remote server, receiving on the one or more processing devices local to the user the one or more assessment modules;

updating the one or more processing devices local to the user to store the one or more assessment modules as executable instructions; and executing one or more of the received assessment modules to analyze the data to check the initial determination of the health condition wherein the executing of the one or more received assessment modules includes executing instructions to collect additional data from the one or more sensors of the respiratory system.

2. The method of claim 1, wherein:

the data is health data associated with the user using the respiratory system; and the one or more assessment modules are one or more health assessment modules.

3. The method of claim 2, wherein the health condition includes at least one of a heart condition, edema, hypertension, chronic obstructive pulmonary disease, atrial fibrillation, drug-resistant hypertension, diabetes, insomnia, overlap of obstructive sleep apnea and chronic obstructive pulmonary disease, obstructive sleep apnea, central sleep apnea, mixed apnea, hypopnea, chronic heart failure, stroke, obesity, metabolic syndrome, depression, coronary artery disease, asthma, periodic limb movement (PLM), Restless Leg Syndrome (RLS), Sleep-Disordered Breathing (SDB), Cheyne-Stokes Respiration (CSR), respiratory insufficiency, Obesity Hyperventilation Syndrome (OHS), Neuromuscular Disease (NMD), and/or chest wall disorders.

4. The method of claim 2, wherein the health data of the user includes therapy data collected during respiratory system operation, duration of respiratory therapy, user interface data, facial feature data, user sensor data, sleep stage information, apnea hypopnea index, user demographic information, user physiological data, operational data of the respiratory system, or any combination thereof.

5. The method of claim 1, wherein the initial determination of the health condition includes determining if there is likely adverse effects therefrom.

6. The method of claim 1, wherein the analysis of the data by the one or more received assessment modules includes assessing if the health condition is present.

7. The method of claim 6, wherein the analysis of the data by the one or more received assessment modules includes assessing if the user is likely experiencing adverse effects from the health condition determined to be present.

8. The method of claim 1, wherein the transmitted command to provide one or more assessment modules includes an instruction to provide at least one additional module to obscure a specific assessment module associated with a determined health condition.

9. The method of claim 1, wherein the received one or more assessment modules includes at least one additional module to obscure a specific assessment module associated with a determined health condition.

10. The method of claim 1, wherein the data includes historical data collected by the one or more processing devices local to the user.

11. The method of claim 1, wherein the data includes real-time data collected by the one or more processing devices.

12. The method of claim 1, wherein the one or more processing devices local to the user include a respiratory device of the respiratory system, an electronic device associated with the respiratory system, or both.

13. The method of claim 12, wherein the electronic device is a mobile device, and the mobile device and the respiratory system are wirelessly connected.

14. The method of claim 1, wherein transmission of the one or more assessment modules is implemented by a respiratory device of a respiratory system, an electronic device associated with the respiratory system, or both.

15. The method of claim 1, wherein the one or more assessment modules is a mobile device app.

16. The method of claim 1, further comprising preparing a de-identified summary report based on (i) the data, (ii) the initially determined health condition or (iii) both (i) and (ii).

17. The method of claim 16, further comprising transmitting the de-identified summary report from the one or more processing devices local to the user for receipt by the remote server or a different server.

18. The method of claim 17, further comprising receiving an input from the user on the one or more processing devices local to the user, the input indicating an authorization to transmit the de-identified summary report to the remote server or the different server.

19. The method of claim 17, further comprising receiving an input from the user on the one or more processing devices local to the user, the input indicating an authorization to transmit a portion of the de-identified summary report to the remote server or the different server.

20. The method of claim 1, wherein the one or more assessment modules include a machine learning algorithm for analyzing select data.

21. A system for determining a health condition of a user of a respiratory system, the system comprising:

a control system including one or more processors; and a memory having stored thereon machine readable instructions;

wherein the one or more processors execute the machine executable instructions in the memory to:

collect and store in the memory data generated by one or more sensors of the respiratory system;

analyze the data to make an initial determination of a health condition associated with the user of the respiratory system, the initial determination including assigning a confidence level to the health condition;

in response to the confidence level meeting a confidence level threshold, transmit a command for receipt by a remote server to provide one or more assessment modules including instructions for analyzing the data to further assess the initially determined health condition;

in response to the one or more assessment modules being provided by the remote server, receive the one or more assessment modules;

store the one or more assessment modules as executable instructions; and execute one or more of the received assessment modules to analyze the data to verify check the initial determination of the health condition, wherein the executing of the one or more received assessment modules includes executing instructions to collect additional data from the one or more sensors of the respiratory system.

* * * * *